United States Patent [19]
Koide et al.

[11] Patent Number: 5,439,579
[45] Date of Patent: Aug. 8, 1995

[54] SENSOR PROBE FOR MEASURING HYDROGEN CONCENTRATION IN MOLTEN METAL

[75] Inventors: Kunihiro Koide, Nagoya; Tamotsu Yajima, Gifu, both of Japan

[73] Assignee: Tokyo Yogyo Kabushiki Kaisha, Tokyo, Japan

[21] Appl. No.: 981,873

[22] Filed: Nov. 25, 1992

[30] Foreign Application Priority Data

| | | | |
|---|---|---|---|
| Nov. 26, 1991 | [JP] | Japan | 3-310984 |
| Dec. 27, 1991 | [JP] | Japan | 3-347383 |
| Dec. 27, 1991 | [JP] | Japan | 3-347384 |
| Dec. 27, 1991 | [JP] | Japan | 3-347385 |
| Dec. 27, 1991 | [JP] | Japan | 3-347386 |
| Dec. 27, 1991 | [JP] | Japan | 3-347387 |
| Dec. 27, 1991 | [JP] | Japan | 3-347388 |
| Jan. 28, 1992 | [JP] | Japan | 4-013468 |
| Jan. 28, 1992 | [JP] | Japan | 4-013469 |
| Jan. 28, 1992 | [JP] | Japan | 4-013470 |

[51] Int. Cl.[6] .............. G01N 27/406; G01N 27/411
[52] U.S. Cl. ............................. 204/422; 204/153.1; 204/400
[58] Field of Search .................. 204/421-429, 204/153.1, 400

[56] References Cited

U.S. PATENT DOCUMENTS

| | | | |
|---|---|---|---|
| 3,486,997 | 12/1969 | Petersen | 204/435 |
| 3,565,769 | 2/1971 | Holden et al. | 204/153.1 |
| 3,598,711 | 8/1971 | Flais | 204/427 |
| 3,657,096 | 4/1972 | Proctor | 204/435 |
| 3,773,641 | 11/1973 | Fitterer | 204/423 |
| 3,791,954 | 2/1974 | Noda et al. | 204/423 |
| 3,864,231 | 2/1975 | Richardson | 204/422 |
| 3,871,981 | 3/1975 | Flais et al. | 204/427 |
| 4,007,106 | 2/1977 | Hone et al. | 204/423 |
| 4,151,060 | 4/1979 | Isenberg | 204/428 |
| 4,430,192 | 2/1984 | Maeda | 204/427 |
| 4,627,892 | 12/1986 | Worrell et al. | 204/422 |
| 4,882,032 | 11/1989 | Tiwari | 204/422 |

FOREIGN PATENT DOCUMENTS 2186090 8/1987 United Kingdom.

OTHER PUBLICATIONS

Patent Abstracts of Japan, vol. 13, No. 87, (P-835), Feb. 28, 1989, JP-A-63 269 053, Nov. 7, 1988, I. Hironari, et al., "Reference Substance For Apparatus For Measuring Concentration of Hydrogen Or Steam Contained In Molten Metal Or Gas".

Hackh's Chemical Dictionary, 4th ed., (1969), pp. 610-611.

Primary Examiner—T. Tung
Attorney, Agent, or Firm—Oblon, Spivak, McClelland, Maier & Neustadt

[57] ABSTRACT

On the inner surface of sensor element made of proton conductive solid electrolyte with perovskite structure and enclosed at its lower end, a reference electrode constituted of porous electrode is formed, and a measuring electrode constituted of porous electrode is formed on the outer surface thereof. And, the reference electrode and the measuring electrode are gas-tightly separated by sealing material. The sensor prove is inserted into ceramic sensor holding cup and both are fixed in such a way that a part of the measuring electrode extrude into said holding cup. Then, by dipping the holder into molten metal by facing its opening part downwards, a space contacting with molten metal is enclosed in the holding cup.

Thereby, reduction of solid electrolyte constituting the sensor element can be prevented, and hydrogen concentration in molten metal can be accurately measured without direct dipping the sensor element into molten metal. Thereby, it is possible to provide a sensor probe and a method for measuring hydrogen concentration in which hydrogen concentration can be continuously measured for long period and an apparatus with smaller size can be made.

6 Claims, 22 Drawing Sheets

SENSOR PROBE FOR MEASURING HYDROGEN CONCENTRATION IN MOLTEN METAL

BACKGROUND OF THE INVENTION

The present invention relates to a sensor probe for measuring hydrogen concentration in molten metal and method for measuring hydrogen concentration in molten metal using said sensor probe.

Conventional methods for measuring hydrogen concentration in molten metal are (1) the initial bubble method calculating the amount of hydrogen gas based on the pressure and temperature of sample at the time first bubble was formed on the surface of sample under reduced pressure, (2) the reduced pressure solidification method measuring the amount of hydrogen gas based on observation of formation of bubbles in the sample solidified under reduced pressure, comparing the specific gravity with that of the standard and the bubble formation on the cross section of the sample, and (3) the Telegas method injecting a small amount of gas into molten metal, collecting discharged gas after circulated in said molten metal and analyzing hydrogen gas in said discharged gas using a gas chromatography after the distribution of hydrogen gas in said discharged gas reached its equilibrium state.

These methods, however, have several disadvantages such as too much time consuming to practically use at the casting site, lower accuracy, larger size of equipment and too much cost for determination.

The present inventors have provided a method for measuring hydrogen concentration in molten metal by constituting galvanic cell type hydrogen sensor using solid electrolyte, $SrCe_{0.95}Yb_{0.05}O_{3-x}$ which shows proton conductivity at high temperature and based on electromotive force generated by the difference of hydrogen activity between the partial pressure of hydrogen on the reference electrode of said sensor and the hydrogen concentration in molten metal measured using said hydrogen sensor. According to this method, there are several advantages such that cost for measuring hydrogen concentration is lower, measuring process can be completed within shorter time, changes of hydrogen concentration in molten metal can be measured continuously as electromotive force, and the like.

However, this method has a disadvantage that continuous operation for longer time is difficult because solid electrolyte is reduced by the molten metal and oxide layer is formed on the interface between the solid electrolyte and the molten metal in case of molten metal having very low partial pressure of oxygen in equilibrium state in molten metal, particularly aluminum. That is, when sensor probe was dipped directly in molten metal for measuring hydrogen concentration in molten metal using proton conductive solid electrolyte, insulating oxide layer formed on the interface between molten metal and solid electrolyte in range of temperature from 400° to 1100° C. for use of sensors disturbs measurement of hydrogen concentration.

SUMMARY OF THE INVENTION

The object of the present invention is to provide a sensor probe for measuring hydrogen concentration in molten metal which can measure hydrogen concentration in molten metal without dipping the measuring part of sensor element directly into molten metal in order to prevent reduction of solid electrolyte constituting said sensor element and a method for measuring hydrogen concentration using said sensor probe.

A sensor probe for measuring hydrogen concentration in molten metal according to the present invention (hereinafter "the first sensor probe") has an element made of proton conductive solid electrolyte with perovskite structure and enclosed at one end. On the inner surface of said element, a reference electrode constituted of porous electrode is formed, and a measuring electrode constituted of porous electrode is formed on the outer surface of said element. The circumferences of said reference electrode and measuring electrode are separated from each other by sealing material. And, a ceramic sleeve or holding cup partially covers the outside of said sensor element so that at least a part of said measuring electrode of the outside surface of said element is extruded to the inside of said sleeve or holding cup.

Also, according to the method for measuring hydrogen concentration in molten metal using said first sensor probe, hydrogen concentration in gas atmosphere enclosed in the space contacting with molten metal in said sleeve or holding cap can be measured by said first sensor probe as galvanic electromotive force between said reference electrode and measuring electrode after hydrogen concentration in said gas atmosphere reached its equilibrium state with that in said molten metal by dipping said sleeve or holding cup of said first sensor probe from its opening part into said molten metal and thereby the concentration of hydrogen dissolved in said molten metal can be obtained.

Another sensor probe for measuring hydrogen concentration in molten metal according to the present invention (hereinafter "the second sensor probe") has a porous ceramic cup, in place of said sleeve or holding cup of the first sensor probe, covering said sensor element to form a space between said element and ceramic cup. This cup allows only gas to permeate, but not for molten metal.

In other sensor probe for measuring hydrogen concentration in molten metal according to the present invention (hereinafter "the third sensor probe"), a reference electrode consisted of porous electrode is formed on the outer surface of an element consisted of proton conductive solid electrolyte with perovskite structure and enclosed at its one end, and a measuring electrode consisting of porous electrode is formed on the inner surface of said element. And, said element is held by holding material or a sleeve covering the element so that the exposed tip of this element is slightly extruded in the enclosure. Said reference electrode and measuring electrode are separated each other by sealing material.

According to the method for measuring hydrogen concentration in molten metal using this third sensor probe, said element is placed in molten metal by partially dipping the opening part of said element in molten metal, and enclosed atmosphere contacting with the surface of the melt bath of molten metal is formed inside said element. Thereby, hydrogen concentration in molten metal can be measured in similar way as aforementioned.

Said proton conductive solid electrolyte with perovskite structure has composition such as $SrCe_{0.95}Yb_{0.05}O_{3-x}$, $BaCe_{0.9}Nb_{0.1}O_{3-x}$, $CaZr_{0.9}In_{0.1}O_{3-x}$ and the like. And, said sleeve or holding cup is formed with gas-impermeable and non-porous ceramic material. In case sealing is made in the time of manufacturing the sensor, said sealing material may be a non-porous glass sealing material having thermal expansion coefficient in range of $8.0 \times 10^{-6}$ to $10.0 \times 10^{-6}/°C$. close to those ($8.5 \times 10^{-6}$ to $9.8 \times 10^{-6}/°C$.) of said solid electrolyte, for example $SrCe_{0.95}Yb_{0.05}O_{3-x}$, $CaZr_{0.9}In_{0.1}O_{3-x}$, $BaCe_{0.95}Y_{0.05}O_{3-x}$ and the like in temperature range from 300° to 1100° C. at the time of use of sensor and having the fluidization point higher than the maximum temperature for use of sensor. On the other hand, in case sealing is made just before use of sensor, it is desirable to use a non-porous glass sealing material having the softening temperature lower than use temperature of sensor and the fluidization point higher than use temperature of sensor.

In this invention, by dipping said sensor holder, said sleeve (for the first sensor probe) or said sensor element (for the third sensor probe) facing its opening part downward, or said cup (for the second sensor probe) into molten metal, the atmosphere contacting with molten metal is enclosed in said sensor holder, sleeve, sensor element or cup. Then, the amount of hydrogen gas released in this atmospheric gas from molten metal is measured by the sensor element as hydrogen partial pressure in the atmospheric gas.

This principle for measuring hydrogen concentration is based on detecting electromotive force of galvanic cell using proton conductive solid electrolyte. Thus, by measuring hydrogen concentration in the high temperature portion near by the surface of molten metal using the sensor probe for measuring dissolved hydrogen concentration, hydrogen concentration in molten metal can be measured from hydrogen concentration obtained when hydrogen concentration in the atmosphere reached in its equilibrium state.

Hydrogen concentration cell type hydrogen sensor using solid electrolyte showing proton conductivity works stably at higher temperature and shows electromotive force close to the theoretical value given by following formula (1):

$$E = (RT/2F) ln[P_{H2}(1)/P_{H2}(2)] \quad (1)$$

where, E stands for electromotive force (V), R for the gas constant, F for Faraday constant, T for the absolute temperature, $P_{H2}(1)$ for hydrogen partial pressure in the atmosphere separated by the sensor holding cup and the like and $P_{H2}(2)$ for hydrogen partial pressure on the reference electrode.

The equilibrium relationship holds between hydrogen concentration in molten metal and hydrogen partial pressure over the surface of melt bath of molten metal, and follows Sieverts' rule expressed by the following equation (2).

$$S = K(P_{H2})^{\frac{1}{2}} \quad (2)$$

where, S stands for hydrogen concentration in its equilibrium state, K for the constant and $P_{H2}$ for hydrogen partial pressure over the surface of molten metal.

As evidenced by the equation (2), by measuring hydrogen partial pressure in the atmosphere contacting with molten metal, concentration of the hydrogen dissolved in molten metal can be measured.

Generally, hydrogen concentration in molten metal depends on both hydrogen partial pressure contacting with said molten metal and temperature of said molten metal and follows to Sieverts' rule and Henry's rule.

Therefore, Hydrogen concentration S is expressed by the following equation (3):

$$log\, S = A - (B/T) + (\tfrac{1}{2}) log\, (P_{H2}) \quad (3)$$

where, A and B stand for the constant depending on composition of metal, respectively.

Then, as shown in FIG. 2 for example, by dipping the opening part of the holding cup into molten metal, the space occupied with atmospheric gas contacting with molten metal is formed between this holding cup and the sensor element consisted of solid electrolyte, and partial pressure of hydrogen gas released in this atmosphere from molten metal can be measured using the sensor probe for measuring hydrogen concentration according to this invention. Using said equation (1), hydrogen partial pressure $P_{H2}$ can be obtained from electromotive force generated between the reference electrode and the measuring electrode of this sensor probe, then hydrogen concentration S can be obtained by substituting this hydrogen partial pressure into the equation (3).

Thus, according to the present invention, hydrogen concentration in molten metal can be continuously measured for longer period without direct contact of the sensor element made of solid electrolyte with molten metal.

According to the present invention, hydrogen concentration in said molten metal can be measured by only dipping the holder and the like of the sensor probe into molten metal (melt bath) and allows continuous measurement for longer period because the whole sensor element or at least the electromotive force measuring part of the sensor probe does not contact with molten metal. In addition, because hydrogen concentration in molten metal can be measured by only detecting the electromotive force of the sensor element of sensor probe, it allows to make the size of measuring equipment smaller and to improve operational efficiency for use during the actual casting process. Furthermore, it is possible to reduce running cost necessary for measuring because gas circulation as required for the Telegas method is not needed. Thus, according to this invention, it is possible to provide an equipment for measuring hydrogen concentration in molten metal with smaller size, high accuracy and high reliability.

Also, the Telegas method, although has a reputation for accurate measurement, can not be applied to the situation with fast flow of molten metal such as discharged gas treatment process. However, the sensor probe related to the present invention can be applied, without any difficulty, even to such situation with fast flow of molten metal to measure hydrogen concentration, therefore it has a wider application fields, and the present invention provides a very useful tool to all technical fields requiring the determination of hydrogen concentration.

DETAILED DESCRIPTION OF THE PREFERRED EMBODIMENTS

Figure 1:
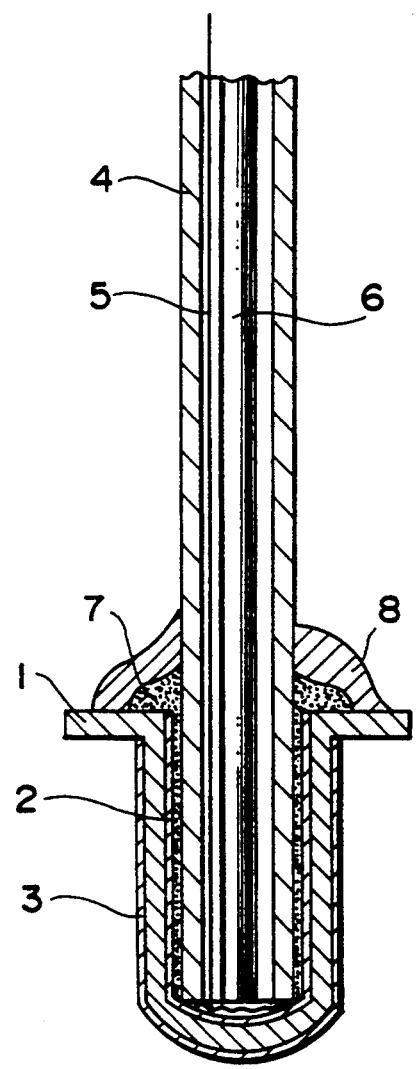
FIG. 1 is a sectional view of a sensor element of the sensor probe for measuring dissolved hydrogen concentration provided in accordance with the first embodiment of the present invention.
Figure 2:
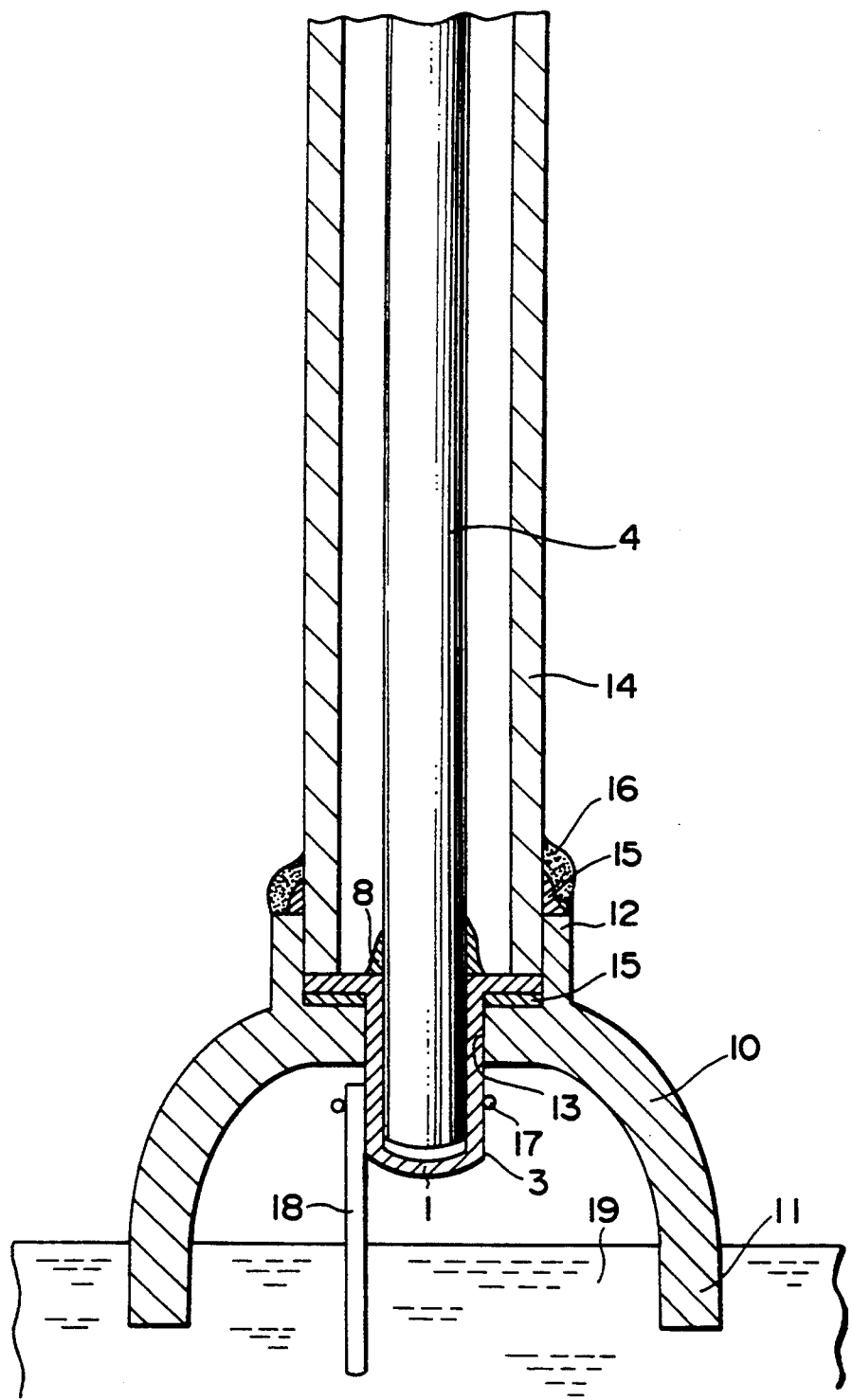
FIG. 2 is a sectional view of a sensor probe incorporated with said sensor element provided in accordance with the first embodiment of the invention.

Referring to the drawings attached, the first embodiment of the present invention will be described in detail. As shown in FIGS. 1 and 2, a sensor element 1 is formed as a tube enclosed at the one end. This sensor element 1 consists of proton conductive solid electrolyte with perovskite structure, for example $SrCe_{0.95}Yb_{0.05}O_{3-x}$, $CaZr_{0.9}In_{0.1}O_{3-x}$, $BaCe_{0.95}Y_{0.05}O_{3-x}$ and the like. Both on the inner surface and the outer surface of said sensor element 1, a reference electrode 2 and a measuring electrode 3, both made of Pt, Ni, conductive oxides or the like for example, are formed by seizure or baking.

One end of a mullite tube 4 for introducing the reference gas (gas containing a constant concentration of hydrogen) is inserted into said sensor element 1. A lead wire 5 made of Pt, Ni or the like is inserted into said tube 4. Further, a mullite tube 6 painted with metal paste such as Pt, Ni or the like is inserted into said tube 4, and said lead wire 5 is pushed by the surface of said tube 6 painted with said metal paste towards said porous reference electrode 2 so that said porous reference electrode 2 is electrically connected to said lead wire 5.

In addition, powdered glass sealing material 7 is placed on the opening part of the sensor element 1 and in the space between said tube 4 and said porous reference electrode 2, and this glass sealing material 7 is covered by ceramic adhesive 8 so that the sensor element 1 is firmly fixed to the tube 4. By this glass sealing material 7, the reference electrode 2 is separated gastightly from outside atmosphere and also the atmosphere around the measuring electrode 3.

As shown in FIG. 2, sensor element 1 constructed as mentioned above is fixed to a holding cup 10 made of ceramic such as $Si_3N_4$ and the like. This holder 10 is provided with a fixing part 12 on the opposite outer side of opening part 11, and a hole 13 is provided at the center of said fixing part 12 which permits insertion of sensor element 1. And, sensor element 1 is inserted into the holder 10 so that the outer surface of said sensor element 1 extends into the holder 10. Furthermore, a mullite ceramic tube 14, for example, covering the outer surface of the tube 4 is placed with its lower end on the fixing part 12 of the holder 10, and the tube 14 is fixed with the ceramic adhesive 16 to the holder 10. Glass sealing material 15 is placed between the brim of the sensor element 1 and the central outer surface of the holder 10 and also between the fixing part 12 and the outer surface of the tube 14 to keep these parts in gas tight.

And, on the measuring electrode 3 of the outer surface of the sensor element 1, an outer electrode 18 is firmly fixed by a lead wire 17 to make electrical contact with measuring electrode 3. This outer electrode 18 is made of material which is not reactive with a melt bath 19.

Then, a method for measuring hydrogen concentration in molten metal, molten aluminum for example, using a sensor probe constructed as mentioned above will be described. As shown in FIG. 2, the opening part 11 of the holding cup 10 is dipped into the melt bath 19 to form a space between the inner surface of the holder 10 and the melt bath 19 in the holder 10. The measuring electrode 3 is placed in this space, avoiding direct contact of the sensor element 1 to the melt bath 19. By dipping the outer electrode 18 connecting to the measuring electrode 3 into the melt bath 19, the measuring electrode 3 is electrically connected to the melt bath 19. Thus, the electric potential on the measuring electrode side of the sensor element 1 can be measured through the melt bath 19 of molten aluminum.

Thus, while a part of the holder 10 is being dipped into the melt bath 19, hydrogen dissolved in the melt bath 19 reaches equilibrium with hydrogen gas in the space between the holder 10 and the melt bath 19, and the relationship between the hydrogen concentration S dissolved in the molten metal and the hydrogen partial pressure $P_{H2}$ in said space can be expressed by said equation (3). Therefore, the hydrogen partial pressure $P_{H2}$ can be measured by the sensor element 1 using galvanic electromotive force. That is, by supplying the reference gas to the atmosphere around of the reference electrode 2 through the tube 4, the electromotive force E generated between the measuring electrode 3 contacting with gas in said space and the reference electrode 2 contacting with said reference gas in the sensor element 1 can be detected. Then, using said equation (1), the hydrogen partial pressure $P_{H2}$ over the surface of molten metal is obtained from this electromotive force. The hydrogen concentration S dissolved in the molten metal is then obtained from this hydrogen partial pressure $P_{H2}$ using said equation (3). Thus, the hydrogen concentration in the molten metal can be measured without dipping the sensor element 1 into the molten metal. Therefore, corrosion of the sensor element 1 by the molten metal can be avoided, and dissolved hydrogen concentration can be continuously measured for long period.

Figure 3:
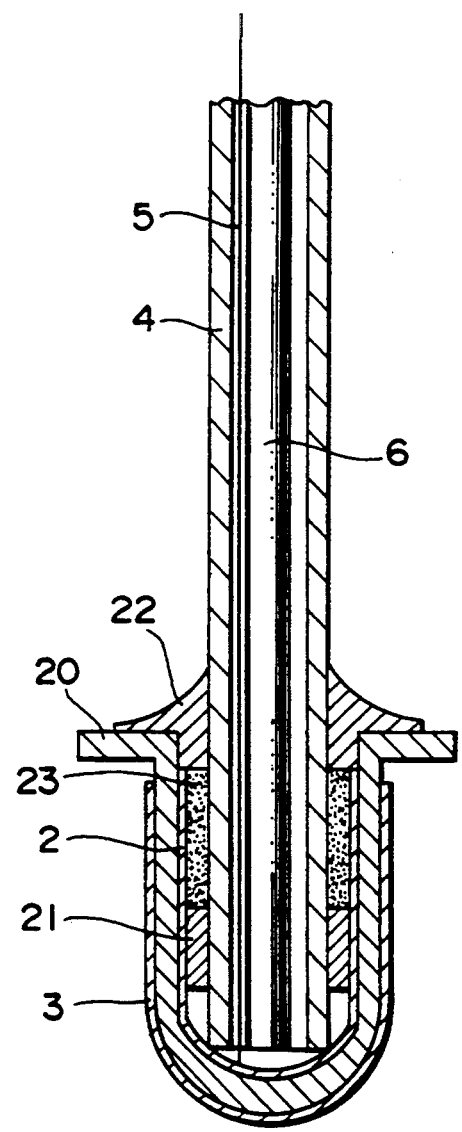
FIG. 3 is a sectional view of a modified form of the sensor element of sensor probe for measuring dissolved hydrogen concentration shown in FIG. 2.

Next, referring to FIG. 3, a modified form of this embodiment will be described. In FIG. 3, all parts essentially same as for FIG. 1 are identified by the same numeral, but will not be described in detail. In this sensor probe, a sensor element 20 has a slightly larger diameter than that of the sensor element 1 shown in FIG. 1, and there exists a slight space between a mullite tube 4 and the inner surface of the sensor element 20. By ceramic adhesive 21 embedded in the space, the sensor element 20 and the tube 4 are fixed. And, powdered glass sealing material 23 is filled in the space between the tube 4 upper the ceramic adhesive 21 and the sensor element 20, and the sensor element 20 and the tube 4 are fixed at the opening part of the sensor element 20 with the ceramic adhesive 22. Thereby, powdered glass sealing material 23 is enclosed by adhesive 22.

Thus constructed sensor probe is also placed in a sensor holder 10 as the sensor probe shown in FIG. 2 and can be used for measuring hydrogen concentration in molten metal as described in the aforementioned embodiment and method with similar effect. Then, the hydrogen concentration in molten metal was measured using a sensor probe manufactured according to this embodiment. Results of this test will be described below. That is, a porous platinum electrode was seized or baked at 900° C. on both the inner and outer surface of a sensor element 1 enclosed at the one end and made of $CaZr_{0.9}In_{0.1}O_{3-x}$, one of proton conductive solid electrolyte with perovskite structure. Then, platinum paste was painted on tubes 4 and 6 made of mullite tubes inserted with a lead wire 5 made of Pt wire, and these tubes 4 and 6 were inserted into the sensor element 1.

Figure 4:
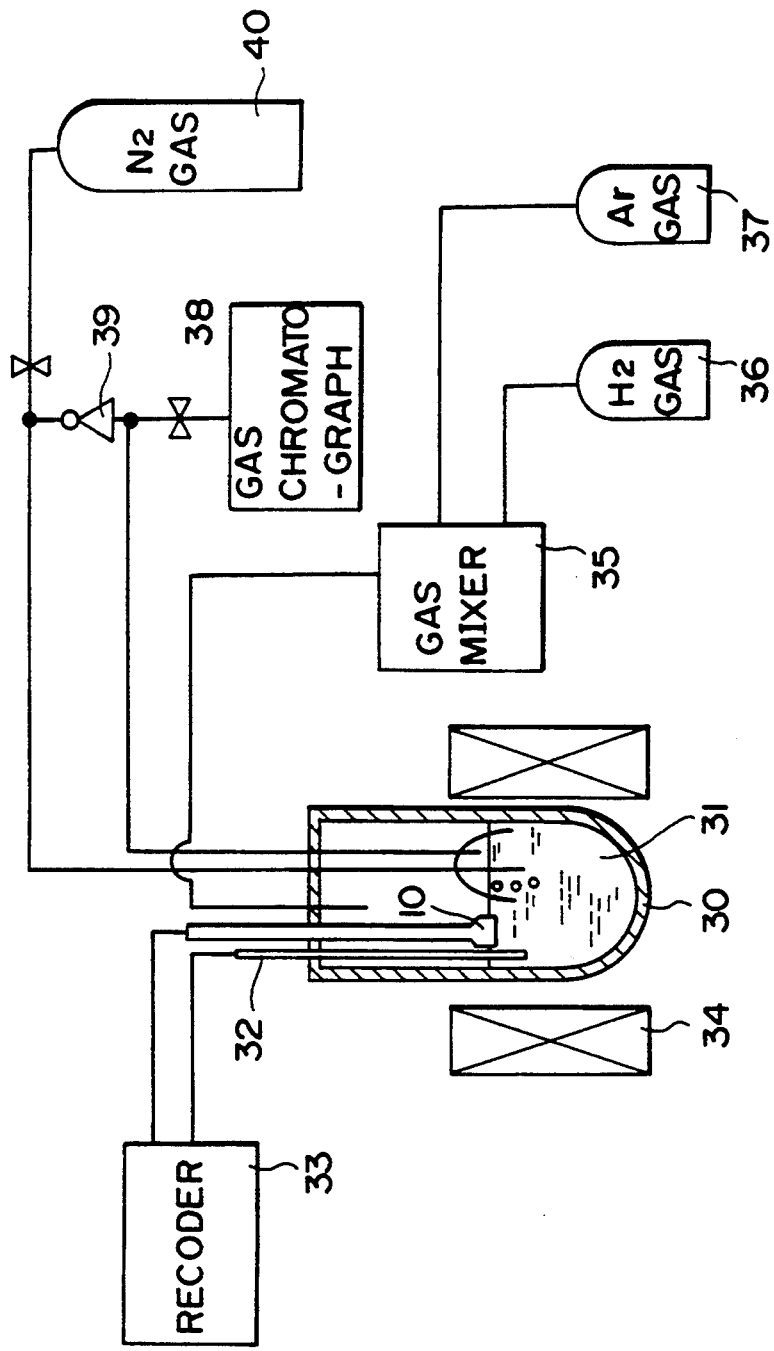
FIG. 4 is a diagram showing an equipment for testing measurement accuracy of the sensor probe of this invention.

Then, powdered glass sealing material 7 (composition: $Na_2O_3.B_2O_3.SiO_2$; thermal expansion coefficient: $9.5 \times 10^{-6}$; softening point: 695° C.; fluidization point: 880° C.) was filled in the space between the mullite tube 4 and the solid electrolyte sensor element 1, and ceramic adhesive 8 was painted. Thus constructed sensor probe was heated in an electric furnace (heating and cooling rate: 5° C./second, keeping 10 minutes at 850° C.) to fuse powdered glass sealing material 7. Then, this probe was fixed to a silicon nitride holding cup 10 using powdered glass sealing material 15 and ceramic adhesive 16. As shown in FIG. 4, the hydrogen concentration in aluminum melt bath 31 melted in a graphite crucible 30 was measured using this sensor probe. The hydrogen partial pressure over the aluminum melt bath 31 was adjusted by introducing a mixture containing Ar gas and hydrogen gas at various rate through a gas mixer 35 connected to an Ar gas source 37 and a hydrogen gas source 36. Thus, the hydrogen concentration in the molten metal was controlled at various values by placing the bath under the atmosphere of various hydrogen partial pressure, and the electromotive force of the sensor element 1 (or 20) was measured under these conditions. The temperature of molten metal and the electromotive force were recorded on a recorder 33. The molten metal in graphite crucible 30 was maintained at constant temperature by heating using a heater 34.

Furthermore, to estimate the measurement accuracy of the sensor probe of this embodiment, the hydrogen concentration in the aluminum melt bath 31 was measured by the Telegas method using a gas chromatographic apparatus 38. In this case, nitrogen gas provided from a nitrogen gas source 40 was bubbled into the molten metal, and when the hydrogen concentration in the atmosphere over the surface of molten metal was reached in equilibrium with the hydrogen concentration in the molten metal, the atmospheric gas was introduced into the gas chromatographic apparatus 38 to measure the hydrogen concentration. Temperature in the melt bath 31 was measured using a K thermocouple and results were in the range of 700°–800° C. The Telegas method used here is known as a method providing highly accurate values in determination of hydrogen concentration in molten metal.

Figure 5:
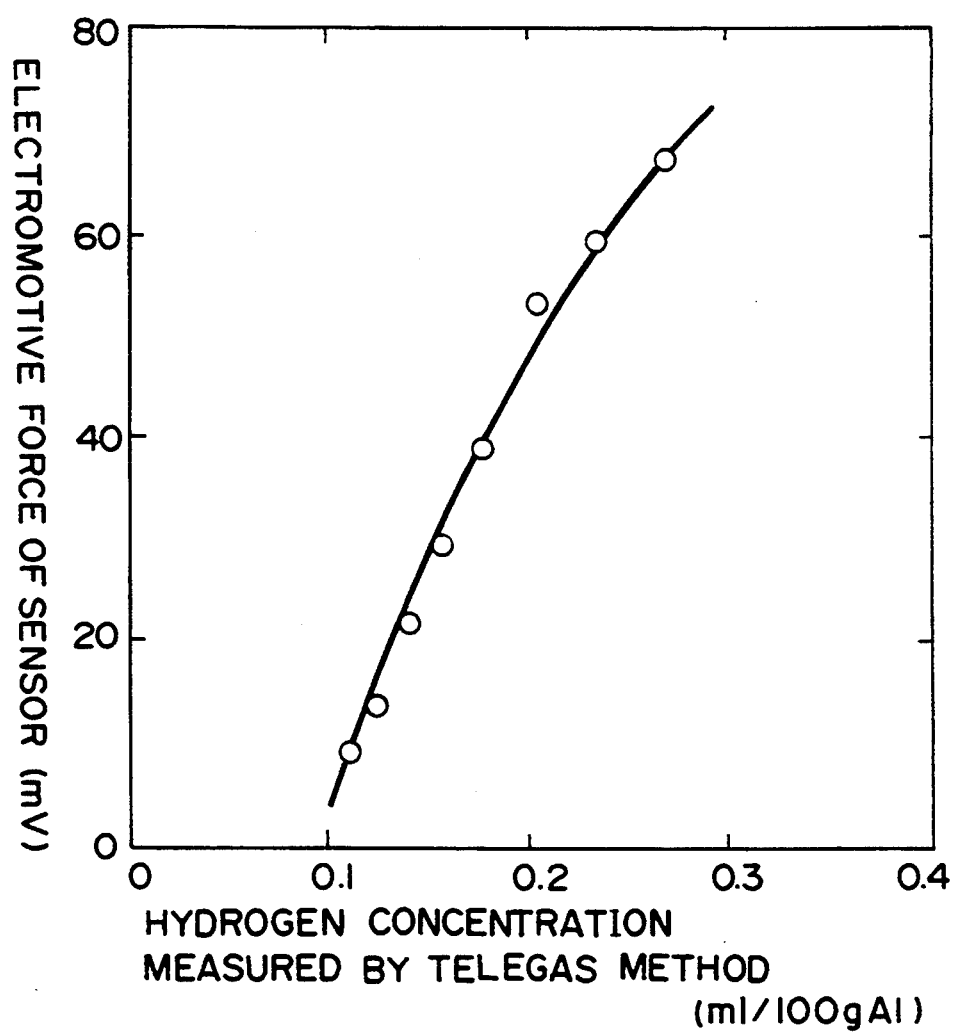
FIG. 5 is a graph showing the relationship between the measured values of hydrogen concentration by the Telegas method and the electromotive forces of the sensor element of this invention.

FIG. 5 shows a graph prepared by plotting hydrogen concentrations measured by the Telegas method on X-axis and electromotive forces of the sensor element on Y-axis. These data were obtained from 99 wt % pure aluminum solution bath maintained at 750° C. According to FIG. 5, there exists very good co-relation between the hydrogen concentration in molten metal measured by the Telegas method and the electromotive force of the sensor element. Similar results can be obtained under different temperature conditions.

Figure 6:
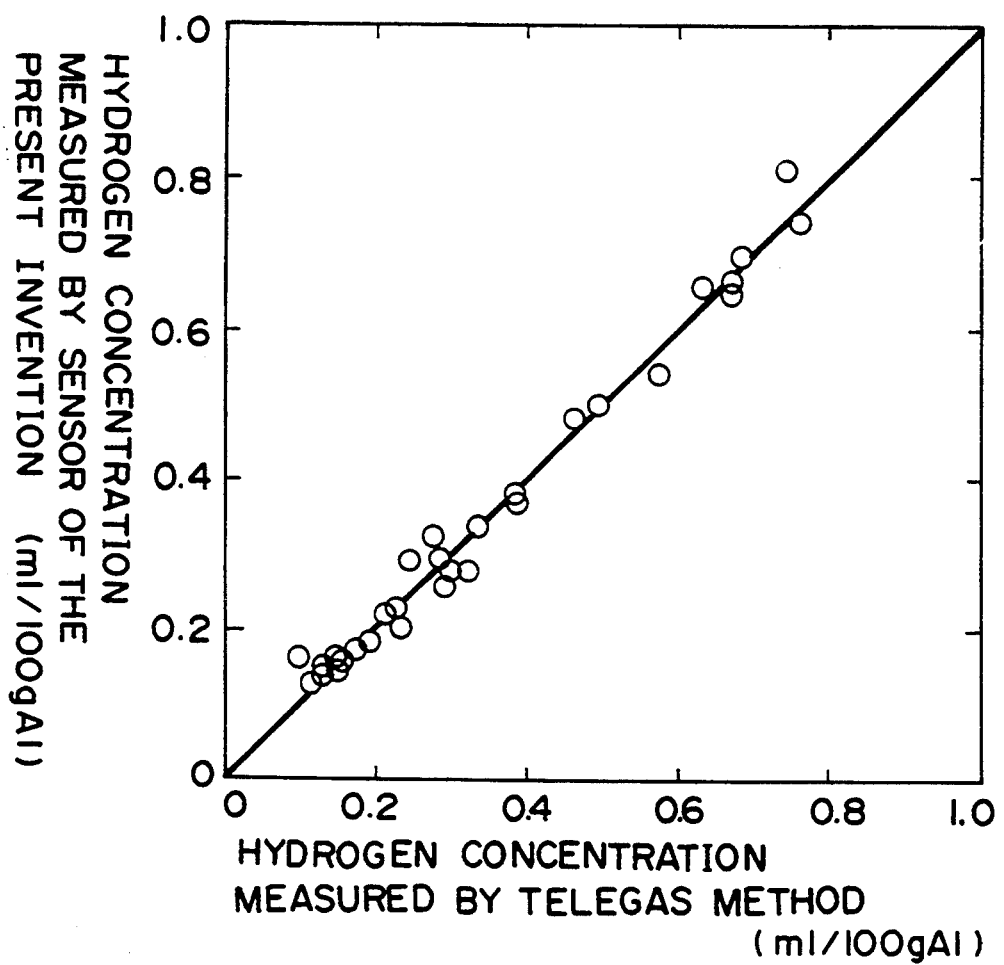
FIG. 6 is also a graph showing the relationship between the measured values of hydrogen concentration by the Telegas method and the electromotive forces of the sensor element of this invention.

FIG. 6 represents a graph prepared by plotting hydrogen concentrations in molten metal measured by the Telegas method on X-axis and hydrogen concentrations measured by the sensor element of this embodiment on Y-axis for comparison. As FIG. 6 clearly shows, there is good agreement between measurements obtained from the Telegas method and those from the sensor of this invention. Therefore, it is understood that the measurements by the sensor probe of this embodiment is highly accurate.

Figure 7:
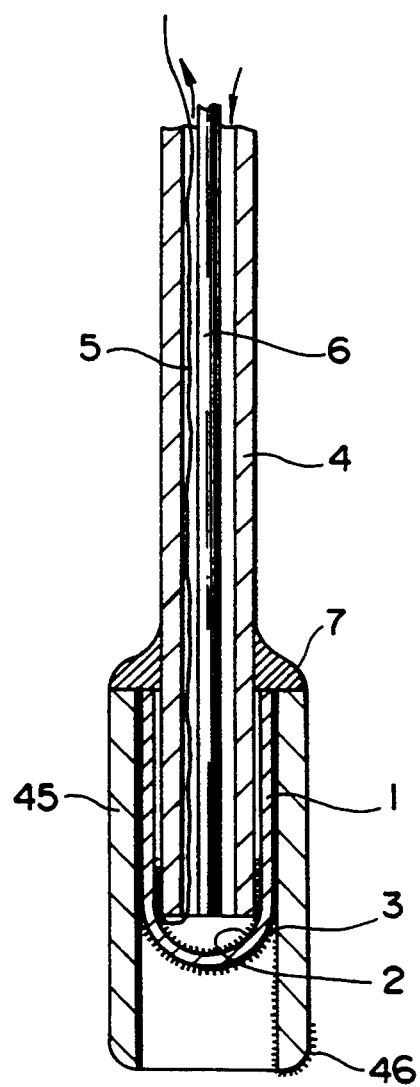
FIG. 7 is a sectional view of a sensor probe for measuring dissolved hydrogen concentration provided in accordance with the second embodiment of the present invention.

FIG. 7 shows a sectional view of a sensor probe for measuring dissolved hydrogen concentration according to the second embodiment of the present invention. In FIG. 7, all parts identical to those shown in FIGS. 1 and 2 are indicated by the same numerals without detail descriptions.

One end of a tube 4 made of a mullite tube for introducing the reference gas (with constant hydrogen concentration) is inserted into a sensor element 1, and a lead wire 5 made of Pt, Ni or the like is inserted into the tube 4. And, a mullite tube 6 is also inserted into this tube 4. The reference gas is supplied to the reference electrode 2 through the passage in the inner tube 6 and discharged from the atmosphere around the reference electrode 2 through the space between the inner tube 6 and the outer tube 4. And, the tube 4 is inserted into the sensor element 1 in a state that metal paste such as Pt, Ni or the like is painted on its lower end part. Thereby, the lower end part of lead wire 5 is caught by the tube 4 and the sensor element 1, and by pushing the lower end part of the lead wire 5 painted with said metal paste to the porous reference electrode 2, the lead wire 5 is being electrically connected to the porous reference electrode 2.

And, a fine ceramic sleeve 45 made of alumina, mullite or silicon nitride, for example, contacts with the outer surface of sensor element 1. This sleeve 45 is longer than the sensor element 1 and its upper level is coordinated to the upper level of the sensor element 1 with extending its lower end far downwards than the lower end of sensor element 1. Powdered glass sealing material 7 is placed in the opening part of the sensor element 1 to fill spaces between the gas inlet tube 4 and the sensor element 1 and the sleeve 45. By this glass sealing material 7, the reference electrode 2 is separated gas-tightly from the outside atmosphere and from the atmosphere around the measuring electrode 3. On inner surface of this sleeve 45, lead 46 made of conductive paste is formed to electrically connect to the measuring electrode 3 of the sensor element 1, and the measuring electrode 3 is connected to a main measuring apparatus (not shown in the drawing) through this lead 46.

Next, the operation of thus constructed sensor probe will be described. By dipping the lower end of the sleeve 45 into molten metal (not shown in this drawing), a space surrounded by the sensor element 1, the sleeve 45 and the surface of molten metal is formed in the sleeve 45. The sensor element 1 is not dipped into molten metal and the measuring electrode 3 is placed in this space.

Thereby, hydrogen dissolved in molten metal reaches equilibrium with hydrogen gas in the space surrounded by the sleeve 45, the sensor element 1 and molten metal, and the relationship between the hydrogen concentration S in molten metal and the hydrogen partial pressure $P_{H2}$ in said space can be expressed by the equation (3). Therefore, the hydrogen partial pressure $P_{H2}$ in this space is measured by the sensor element 1 using galvanic electromotive force. That is, the reference gas is supplied to and circulated around the reference electrode 2 using the tubes 4 and 6, the electromotive force E generated between the measuring electrode 3 contacting with gas in said space and the reference electrode 2 contacting with the reference gas in the sensor element 1 is detected, and the hydrogen partial pressure $P_{H2}$ over molten metal is obtained from this electromotive force using said equation (1). Then, the hydrogen concentration S dissolved in molten metal is calculated from this hydrogen partial pressure $P_{H2}$ using said equation (3). Thus, hydrogen concentration in molten metal can be measured without dipping the sensor element 1 into molten metal. Therefore, corrosion of the sensor element 1 by molten metal can be avoided, and dissolved hydrogen concentration can be continuously measured for long period.

Figure 8:
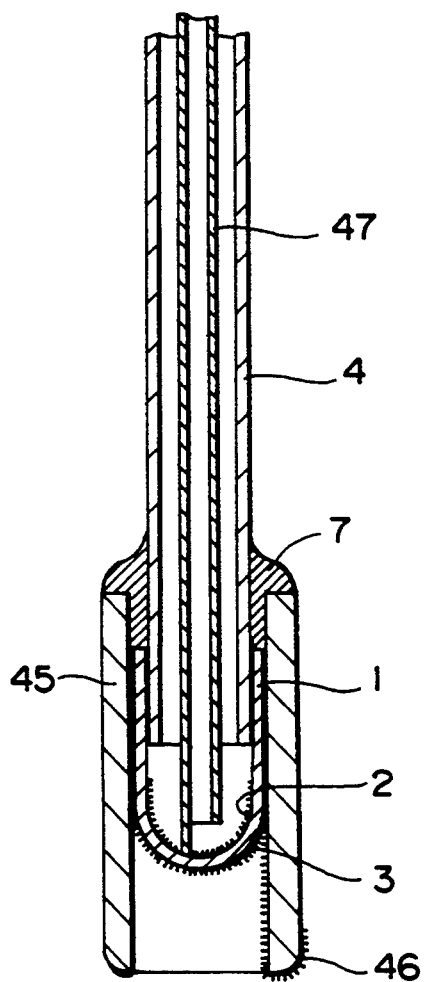
FIG. 8 is a sectional view of a modified form of the sensor probe shown in FIG. 7.

FIG. 8 shows a modified form of this embodiment. In FIG. 8, all parts essentially identical to those shown in FIG. 7 are shown by same numerals without detail description. A tube 47 for discharging the reference gas of this sensor probe is made of stainless steel, therefore it is electroconductive.

Then, by electrically connecting the reference electrode 2 on the inner surface of the sensor element 1 to the tube 47, the reference electrode 2 is electrically connected to a main measuring apparatus through the tube 47. Therefore, the lead wire 5 used in the previous embodiment as shown in FIG. 7 can be eliminated thereby. This embodiment has an effect similar to that of the previous embodiment shown in FIG. 7.

Then, manufacturing of the sensor probe according to the embodiment shown in FIG. 8 and results of measurement of hydrogen concentration in molten metal will be described. First, a porous platinum electrode was seized or baked on the inner and outer surfaces of a sensor element 1 made of $CaZr_{0.9}In_{0.1}O_{3-x}$ of proton conductive solid electrolyte with perovskite structure and enclosed at the one end at temperature of 900° C. Then, an aluminum tube 4 and a stainless steel tube 47 with function as a lead wire were inserted into the sensor element 1.

Next, a mullite sleeve 45 was attached to the sensor element 1 so that its lower end is extending 10 mm downwards from the lower end level of the sensor element 1, and the tube 4, the sensor element 1 and the sleeve 45 were fixed by powdered glass sealing material 7 (composition: $Na_2O_3 \cdot B_2O_3 \cdot SiO_2$; thermal expansion coefficient: $9.5 \times 10^{-6}$; softening point: 695° C.; fluidization point: 880° C.). Thus constructed sensor probe was heated in an electric furnace (heating and cooling rates were 5° C./minute and maintained at 850° C. for 10 minutes) to fuse and fix powdered glass sealing material 7.

Then, using thus constructed sensor probe, the hydrogen concentration in the aluminum melt bath 31 was measured by the apparatus shown in FIG. 4. The reference gas for the sensor element 1 was 1% hydrogen gas. As result, measurements obtained were similar to those shown in FIGS. 5 and 6 which were obtained from the first embodiment shown in FIGS. 1 and 2, and hydrogen concentration in molten metal could be measured in this embodiment.

Figure 9:
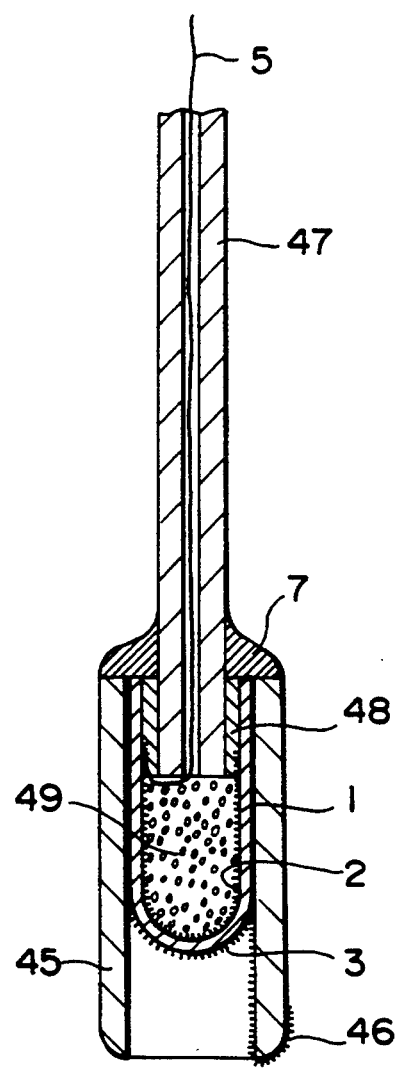
FIG. 9 is a sectional view of a sensor probe for measuring dissolved hydrogen concentration provided in accordance with the third embodiment of the present invention.

Next, the third embodiment of this invention will be described, referring to FIG. 9. In FIG. 9, all parts identical to those referred in FIGS. 7 and 8 are indicated using the same numerals, but they are not described in detail. The lower half of a sensor element 1 is filled with solid reference material 49. And, a ceramic insulating tube 47 is inserted into the upper part of the sensor element 1 to hold the sensor element 1 so that solid reference material 49 is sealed in the sensor element 1 by this insulating tube 47. The insulating tube 47 is fixed to the inner surface of the sensor element 1 by metal paste 48 such as Pt and the like.

A lead wire 5 made of Pt, Ni or the like is inserted into the insulating tube 47. On the lower end part of the insulating tube 47, metal paste such as Pt, Ni or the like is painted, and by catching the lower end part of lead wire 5 with the insulating tube 47 and solid reference material 49, the lead wire 5 is electrically connected to solid reference material 49 by said metal paste.

And, a fine ceramic sleeve 45 made of alumina, mullite or nitride silicon, for example, is connected to the outer surface of sensor element 1. This sleeve 45 is longer than the sensor element 1 and its upper level is coordinated to the upper level of the sensor element 1, so that its lower end is extending downwards than the lower end of sensor element 1. Powdered glass sealing material 7 is placed in the opening part of the sensor element 1 to fill the space between the insulating tube 47, the sensor element 1 and the sleeve 45. By this glass sealing material 7, the reference electrode 2 is separated gas-tightly from the outside atmosphere and from the atmosphere around the measuring electrode 3. On inner surface of this sleeve 45, lead 46 made of conductive paste is formed to electrically connect with the measuring electrode 3 of the sensor element 1, and the measuring electrode 3 is connected to a main measuring apparatus (not shown in the drawing) through this lead 46.

As solid reference material, there are hydroxyapatite $(Ca_{10}(PO_4)_6(OH)_2)$, aluminum phosphate $(AlPO_4)$ and the like as described in Japanese Patent Application Laid Open No. 269053/1988.

Next, the operation of thus constructed sensor probe will be described. By dipping the lower end of the sleeve 45 into molten metal (not shown in FIG. 9), a space surrounded by the sensor element 1, the sleeve 45 and the melt surface is formed in the sleeve 45. The sensor element 1 is not dipped into the molten metal and the measuring electrode 3 is placed in this space.

Thus, as described in the previous embodiment shown in FIG. 7 and 8, by detecting the electromotive force E generated between the electrode 3 contacting with gas in the said space and the reference electrode 2 contacting the solid reference material 49 in the sensor element 1, the hydrogen partial pressure $P_{H2}$ over molten metal can be obtained from this electromotive force according to said equation (1). And, from this hydrogen partial pressure $P_{H2}$, the hydrogen concentration S dissolved in molten metal can be obtained according to said equation (3). Thus, hydrogen concentration in molten metal can be measured without dipping the sensor element 1 into the molten metal. Therefore, corrosion of the sensor element 1 by molten metal can be avoided, and dissolved hydrogen concentration can be continuously measured for long period.

Figure 10:
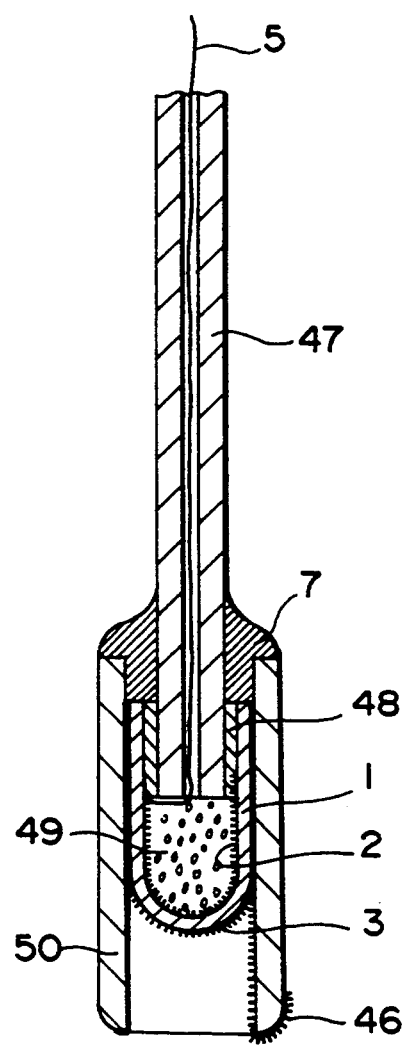
FIG. 10 is a sectional view of a modified form of the sensor probe shown in FIG. 9 of this invention.

FIG. 10 is a sectional view of a modified form of this embodiment. In FIG. 10, all parts essentially identical to those shown in FIG. 9 are shown by same numerals without detail description. This sensor probe has a relatively longer sleeve 50 of which upper part is placed on higher level than the upper part of the sensor element 1. Therefore, glass sealing material 7 covers also the space between the sleeve 50 and the insulating tube 47 to improve its sealing performance. This embodiment has effect similar to that of the previous embodiment shown in FIG. 9.

Then, manufacturing of the sensor probe according to the embodiment shown in FIG. 10 and results of measurement of hydrogen concentration in molten metal will be described. First, a porous platinum electrode 2 and a measuring electrode 3 were seized or baked on the inner and outer surfaces of a sensor element 1 made of $CaZr_{0.9}In_{0.1}O_{3-x}$ and enclosed at the one end at temperature of 900° C. Then, the sensor element 1 was filled with a mixture of $AlPO_4$ and $La_{0.4}Sr_{0.6}CoO_{3-x}$ powders as solid reference material, an aluminum insulating tube 47 inserted with Pt lead wire and painted with Pt paste was inserted into the sensor element 1. Then, a sensor probe was manufactured as described in the previous embodiment shown in FIG. 8.

Then, hydrogen concentration in the aluminum melt bath 31 was measured by the apparatus shown in FIG. 4 using this sensor probe. In this embodiment, results similar to those shown in FIGS. 5 and 6 could be obtained.

Figure 11:
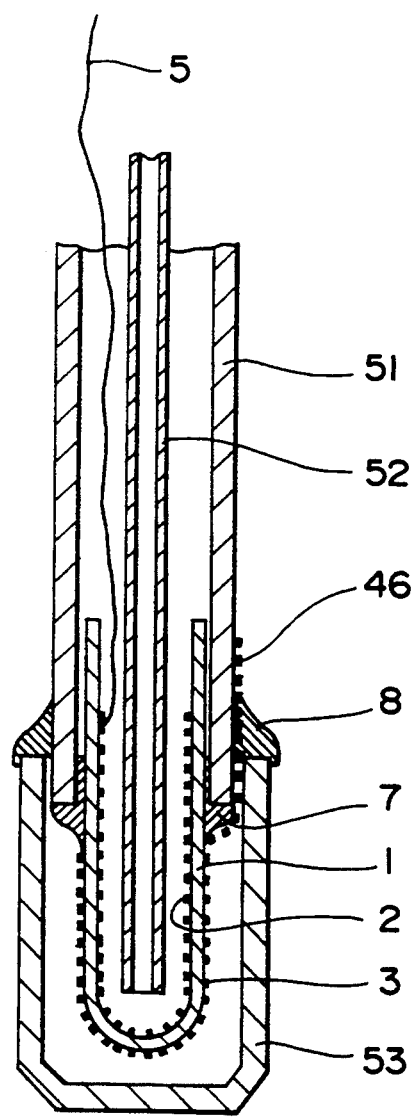
FIG. 11 is a sectional view of a sensor probe for measuring dissolved hydrogen concentration provided in accordance with the fourth embodiment of this invention.

Next, the fourth embodiment of this invention will be described, referring to FIG. 11. The upper part of a sensor element 1 is covered with a part of a fine ceramic tube 51 made of alumina, mullite or silicon nitride, for example, for introducing the reference gas (constant hydrogen concentration) and holding the sensor element, and a lead wire 5 made of Pt, Ni or the like is inserted into this tube 51. This lead wire 5 is electrically connected to the reference electrode 2 on the inner surface of the sensor element 1 by metal paste made of Pt, Ni or the like. And, a mullite tube 52 is inserted into the tube 51. The reference gas is supplied to the reference electrode 2 through the passage in the inner tube 52 and discharged from the atmosphere around the reference electrode 2 through the space between the outer tube 51 and the inner tube 52. And, glass sealing material 7 is placed on the space between the lower end of tube 51 and the sensor element 1, and this glass sealing material 7 is connecting to the tube 51 and the sensor element 1 and also keeping in gas-tight between both parts as well as between the reference electrode 2 and the outside atmosphere. On the outer surface of the tube 51, is painted with conductive paste 46 which is electrically connected to the measuring electrode 3 on the outer surface of the sensor element 1. By this, the measuring electrode 3 is connected to a signal processor through this conductive paste 46.

And, a porous silicon carbide ceramic cup 53 is formed as a tube enclosed at its lower end and fixed to the tube 51 through ceramic adhesive 8 so that its open end is placed on the lower end of the tube 51. This cup 53 is made of porous silicon carbide (SiC) which is difficult to wet with molten metal.

Said porous ceramic cup is made of materials through which molten metal is not permeable but only gas is permeable. As one of such materials, silicon carbide with poor wettability to molten metal can be used. Such material which is poor wettable to molten metal is preferable due to lower permeability of molten metal into the cup. Furthermore, it is preferable to use a material with pore size of 30 μm or less as porous material constituting this cup 53 to ensure prevention of permeability of molten metal.

Then, the operation of thus constructed sensor probe will be described. First, by dipping the porous silicon carbide cup 53 into molten metal (not shown in FIG. 11), a part of formed measuring electrode 3 of a sensor element 1 is placed on lower level than the surface of molten metal. By doing this, the space surrounded by the cup 53, i.e. the space between the cup 53 and the sensor element 1, contacts with molten metal through the cup, and thereby the measuring electrode 3 of the sensor element 1 contacts with this atmosphere.

Thus, hydrogen concentration in molten metal reaches in equilibrium with hydrogen gas in the space surrounded by the cup 53, and the relationship between the hydrogen concentration S in molten metal and the hydrogen partial pressure $P_{H2}$ in said space can be expressed by said equation (3). Then, the hydrogen partial pressure $P_{H2}$ in this space is measured by the sensor element 1 using galvanic electromotive force. That is, by circulating the reference gas around the reference electrode 2 through the tubes 51 and 52, and by detecting the electromotive force E generated between the electrode 3 contacting with gas in said space and the reference electrode 2 contacting with said reference gas in the sensor element 1, the hydrogen partial pressure $P_{H2}$ over the surface of molten metal is measured from this electromotive force according to said equation (1). Then, the hydrogen concentration S dissolved in molten metal is measured from this hydrogen partial pressure $P_{H2}$ according to said equation (3). Thus, the hydrogen concentration in molten metal can be measured without dipping the sensor element 1 into molten metal. Therefore, corrosion of the sensor element 1 by molten metal can be avoided and the dissolved hydrogen concentration can be continuously measured for long period.

Figure 12:
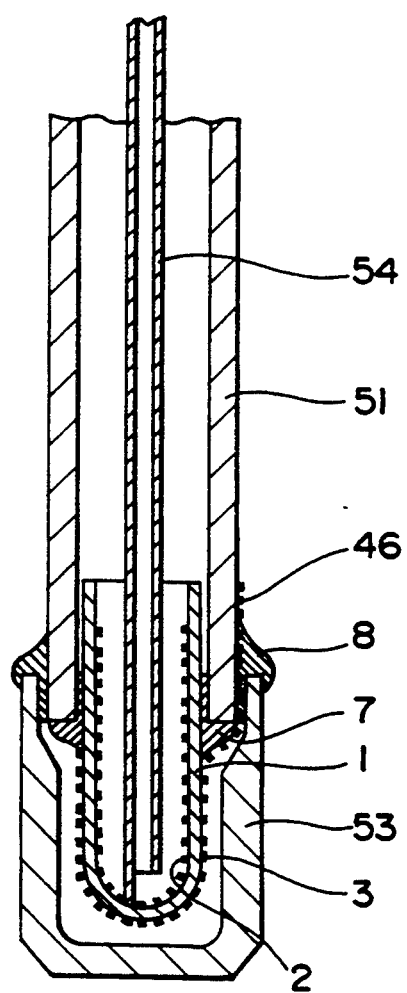
FIG. 12 is a sectional view of a modified form of the sensor probe shown in FIG. 11 of this invention.

FIG. 12 is a sectional view of a modified form of this embodiment. In FIG. 12, all parts essentially identical to those shown in FIG. 11 are shown by same numerals without detail description. A reference gas discharge tube 54 of this sensor probe is made of stainless steel, therefore it is an electroconductive. Then, by connecting electrically the reference electrode 2 on the inner surface of a sensor element 1 to the tube 54, the reference electrode 2 is electrically connected to a main measurement apparatus through the tube 54. Thereby, the lead wire 5 of the previous embodiment shown in FIG. 11 can be eliminated. This embodiment has effect similar to that of the previous embodiment shown in FIG. 1.

Then, manufacturing of the sensor probe according to the embodiment shown in FIG. 12 and results of determination of hydrogen concentration in molten metal will be described. First, an alumina tube 51 was inserted into a sensor element 1 manufactured as the aforementioned, then seized each other using powdered glass sealing material 7 (composition: $Na_2O_3.B_2O_3.SiO_2$; thermal expansion coefficient: $9.5 \times 10^{-6}$; softening point: 695° C.; fluidization point: 880° C.). Then, the sensor element 1 was covered by a porous silicon carbide cup 53 with pore size of 30 μm or less, and this cup was fixed to the tube 51 by ceramic adhesive.

Thus constructed sensor probe was heated in an electric furnace (heating and cooling rate: 5° C./minute; maintained at 850° C. for 10 minutes) to fuse powdered glass sealing material 7, then ceramic adhesive was solidified by cooling down. Then, a stainless steel tube 54 having both functions as gas inlet tube and lead tube was inserted into the sensor element 1, and the lower end of this tube 54 was fixed to the reference electrode 2 to complete the sensor probe.

Then, the hydrogen concentration in the aluminum melt bath 31 was measured using this sensor probe as shown in FIG. 4. As the reference gas in the sensor element 1, 1% hydrogen gas was used. As result, the hydrogen concentration in the molten metal could be measured accurately as described for the sensor probe shown in FIGS. 5 and 6.

Figure 13:
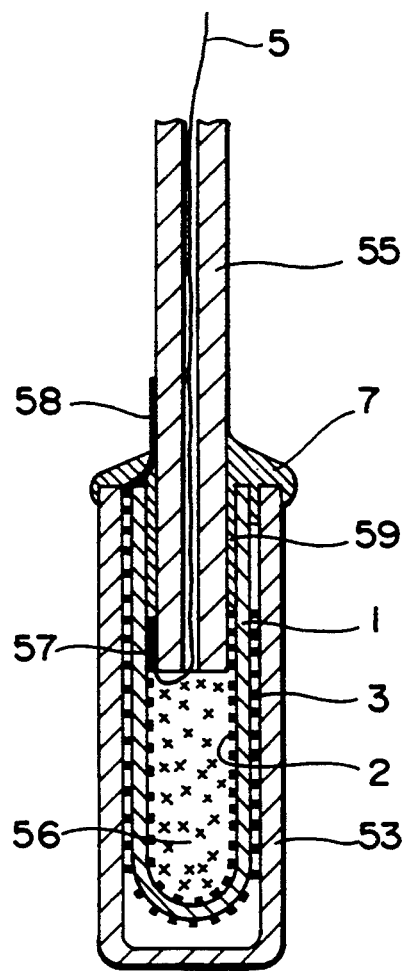
FIG. 13 is a sectional view of a sensor probe for measuring dissolved hydrogen concentration provided in accordance with the fifth embodiment of the present invention.

Next, the fifth embodiment of this invention will be described, referring to FIG. 13. In FIG. 13, all parts identical to those referred in FIGS. 11 and 12 are indicated using the same numerals, but they are not described in detail. The lower end of a ceramic insulating tube 55 for holding a sensor element is inserted into the upper part of the sensor element 1, and the sensor element 1 and the ceramic insulating tube 55 are fixed each other by ceramic adhesive 59. A lead wire 5 made of Pt, Ni or the like is inserted into this insulating tube 55. This lead wire 5 is electrically connected to the reference electrode 2 on the inner surface of the sensor element 1 through metal paste 57 made of Pt, Ni or the like. On the outer surface of the insulating tube 55, is painted with conductive paste 58 so that this conductive paste 58 is electrically connected to a measuring electrode 3 on the outer surface of the sensor element 1. Thereby, the measuring electrode 3 is connected to a main measuring apparatus through this conductive paste 58.

In a space enclosed by the insulating tube 55 in the sensor element 1, as the reference for galvanic electromotive force, solid reference material 56 is filled to contact with the reference electrode 2. As solid reference material 56, there are hydroxyapatite, aluminum phosphate and the like.

And, as previously described, the sensor element 1 is attached to the opening part of a porous ceramic cup 53 with poor wettability to molten metal. And, on both opening parts of this cup 53 and the sensor element 1, glass sealing material 7 is placed, and thereby both the reference electrode 2 and the measuring electrode 3 are sealed in gas-tight from each other and from the outside atmosphere. In this embodiment, the cup 53 is fixed to the sensor element 1 and an appropriate space is formed between the cup 53 and the outer surface at the enclosed part of the sensor element 1.

Next, the operation of thus constructed sensor probe will be described. First, by dipping the porous silicon carbide cup 53 into molten metal (not shown in FIG. 13), a space formed between the sensor element 1 and the cup 53 is placed at lower level than the surface of molten metal. Thereby, the space surrounded by the cup 53; i.e. the space between the cup 53 and the sensor element 1, contacts with molten metal through the cup 53. Therefore, the measuring electrode 3 of the sensor element 1 contacts with this space.

Thus, as described in the previous embodiment shown in FIG. 12, the hydrogen concentration $P_{H2}$ in said space can be measured by the sensor element 1 using galvanic electromotive force. In this case, solid reference material 56 is used as the reference for galvanic electromotive force.

Then, manufacturing of the sensor probe according to the embodiment shown in FIG. 13 and results of determination of hydrogen concentration in molten metal will be described. As solid reference material 56, a mixture of $AlPO_4$ and $La_{0.4}Sr_{0.6}CoO_{3-x}$ powders was used. An alumina insulating tube 55 inserted with Pt lead wire 5 and painted with Pt paste on its lower end was inserted into the sensor element 1 and fixed with ceramic adhesive 59. Then, whole sensor probe 1 was covered with a porous silicon carbide ceramic cup 53 with the average pore size of 15 μm, and it was sealed by powdered glass sealing material 7 (composition: $Na_2O_3B_2O_3$ $SiO_2$; thermal expansion coefficient: $9.5 \times 10^{-6}$; softening point: 695° C.; fluidization point: 880° C.).

Thus constructed sensor probe was heated in an electric furnace (heating and cooling rate: 5° C./minute; maintained at 850° C. for 10 minutes) to fuse powdered glass sealing material 7, then ceramic adhesive was solidified.

Then, the hydrogen concentration in the aluminum melt bath 31 was measured by the apparatus shown in FIG. 4 using this sensor probe. As result, the hydrogen concentration in molten metal could be measured accurately similar to those shown in FIGS. 5 and 6.

Figure 14:
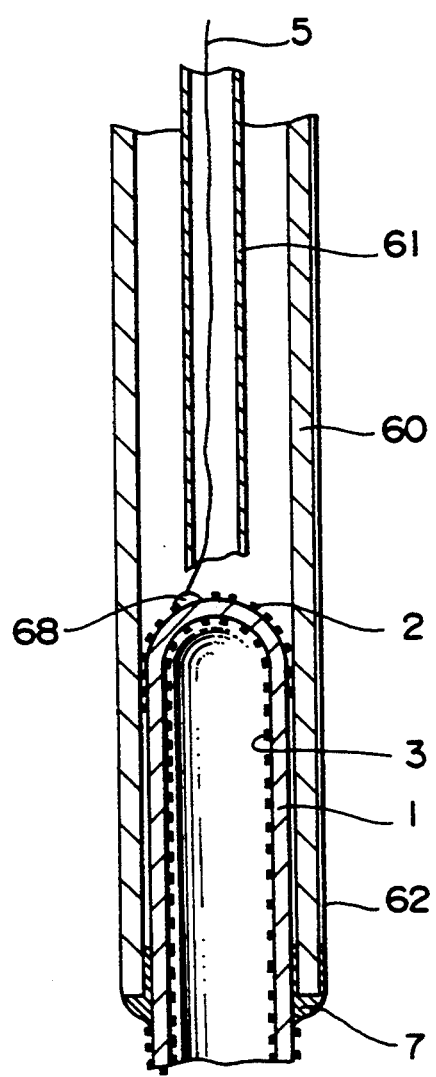
FIG. 14 is a sectional view of a sensor probe for measuring dissolved hydrogen concentration provided in accordance with the sixth embodiment of this invention.

Then, referring to FIG. 14, the sixth embodiment of this invention will be described. In this embodiment, a non-porous ceramic sleeve 60 made of alumina, mullite or silicon nitride for example, is connected to the outer surface of sensor element 1. This sensor element 1 is placed in the sleeve 60 so that its opening lower end is slightly extending from the lower end of the sleeve 60, and the sleeve 60 and the sensor element 1 are fixed to each other at the lower end of the sleeve 60 by glass sealing material 7. By this glass sealing material 7, the reference electrode 2 is provided with a gas-tight seal from the electrode 3 as well as from the outside atmosphere.

On the inner surface of this sleeve 60, lead 62 made of conductive paste is formed to electrically connect to the measuring electrode 3 extending its open part slightly outside of the sensor element 1, and the measuring electrode 3 is connected to a main measuring apparatus (not shown in the drawing) through this lead 62. On the other hand, a part of mullite tube 61 for introduction of the reference gas (at constant hydrogen concentration) is inserted into the ceramic sleeve 60, and a lead wire 5 made of Pt, Ni or the like is inserted into this tube 61. This lead wire 5 is electrically connected to the porous reference electrode 2 through conductive paste 68, and the reference electrode 2 is connected to a main measurement apparatus through the lead wire 5.

Each of the tubes 61 and 60 has a double tube structure. The reference gas is supplied to the reference electrode 2 through the passage in the inner tube 61 and discharged from the atmosphere around the reference electrode 2 through the passage formed between the outer tube 60 and the inner tube 61.

Next, the operation of thus constructed sensor probe will be described. By dipping the lower end of the sensor element 1 made of proton conductive solid reference material into molten metal (not shown in this drawing), a space surrounded by the sensor element 1 and the surface of molten metal is formed in the sensor element 1. Only the lower part of the sensor element 1 is dipped into molten metal and most part of the measuring electrode 3 is placed in said space.

Thereby, hydrogen dissolved in molten metal reaches equilibrium with hydrogen gas in the space surrounded by the sensor element 1 and molten metal, and the relationship between the hydrogen concentration S in molten metal and the hydrogen partial pressure $P_{H2}$ in said space can be expressed by the equation (3). Therefore, the hydrogen partial pressure $P_{H2}$ in this space is measured by the sensor element 1 using galvanic electromotive force. That is, the reference gas is supplied to and circulated around the reference electrode 2 using the tubes 61 and 60, the electromotive force E generated between the measuring electrode 3 contacting with gas in said space and the reference electrode 2 contacting with said reference gas is detected, and the hydrogen partial pressure $P_{H2}$ over molten metal is obtained from this electromotive force using said equation (1). Then, the hydrogen concentration S dissolved in molten metal is calculated from this hydrogen partial pressure $P_{H2}$ using said equation (3). Thus, hydrogen concentration in molten metal can be measured without dipping the sensor element 1 into molten metal. Therefore, corrosion of the sensor element 1 by molten metal can be avoided, and dissolved hydrogen concentration can be continuously measured for long period.

Figure 15:
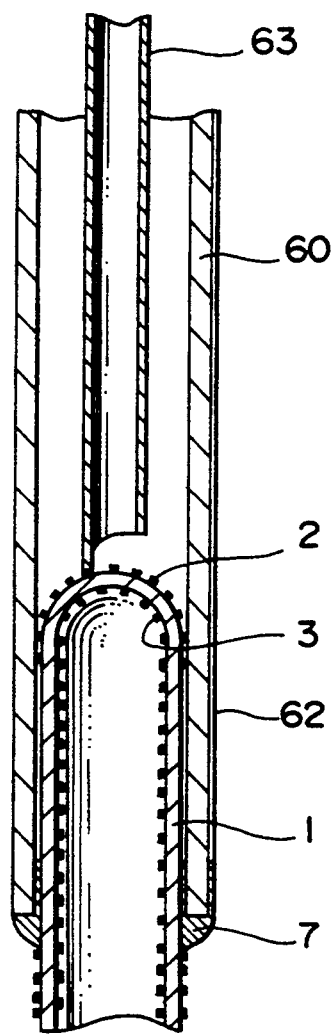
FIG. 15 is a sectional view of a modified form of the sensor probe shown in FIG. 14.

FIG. 15 is a sectional view of a modified form of this embodiment. In FIG. 15, all parts essentially identical to those shown in FIG. 14 are shown by same numerals without detail description. A reference gas discharge tube 63 of this sensor probe is made of stainless steel, therefore it is electroconductive. Then, by connecting electrically the reference electrode 2 on the inner surface of a sensor element 1 to the tube 63, the reference electrode 2 is electrically connected to a main measurement apparatus through the tube 63. Thereby, the lead wire 5 of the previous embodiment shown in FIG. 1 can be eliminated. This embodiment has effect similar to that of the previous embodiment shown in FIG. 1.

Then, manufacturing of the sensor probe according to the embodiment shown in FIG. 15 and results of determination of hydrogen concentration in molten metal will be described. First, on the outer and inner surfaces of said sensor element 1, a porous platinum electrode was seized at 900° C. Then, an alumina tube 60 was fixed on the outside surface of the sensor element 1, and by glass sealing material 7 (composition: $Na_2O_3$.-$B_2O_3.SiO_2$; thermal extension coefficient: $9.5 \times 10^{-6}$; softening point: 695° C.; fluidization point: 880° C.), the tube 60 and the element 1 were fixed. Thus constructed sensor probe was heated in an electric furnace to fuse powdered glass sealing material 7. Then, a stainless steel tube 63 having a function as a lead wire was inserted into the tube 60 and this lead tube 63 was connected to the reference electrode 2.

Then, the hydrogen concentration in the aluminum melt bath 31 was measured using this sensor probe as shown in FIG. 4. As the reference gas in the sensor element 1, 1% hydrogen gas was used. As a result, the same effects as shown in FIGS. 5 and 6 could be obtained.

Figure 16:
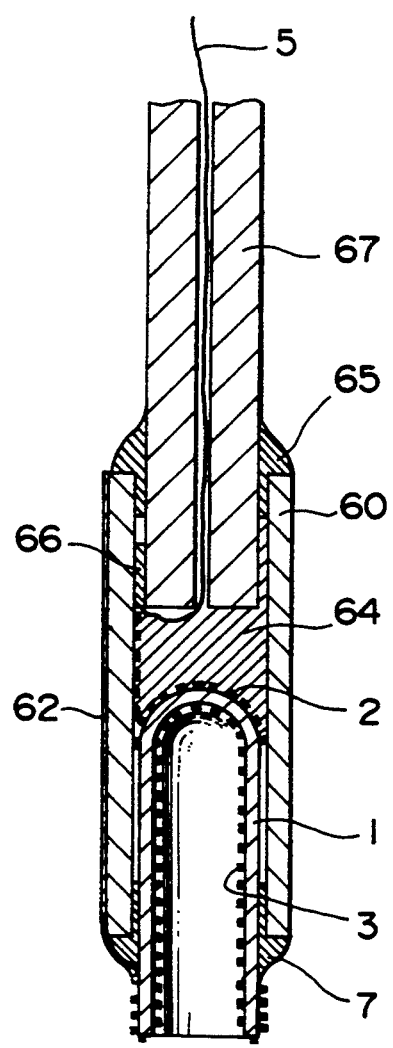
FIG. 16 is a sectional view of a sensor probe for measuring dissolved hydrogen concentration provided in accordance with the seventh embodiment of the present invention.

Then, referring to FIG. 16, the seventh embodiment of this invention will be described. In FIG. 16, all parts identical to those used in FIG. 15 identified with the same numerals used for FIG. 15 and detail description was omitted. As shown in FIG. 16, in the half upper part of a non-porous ceramic sleeve 60 made of alumina, mullite or silicon nitride for example, is inserted with a part of a ceramic insulating tube 67 to hold a sensor, and a lead wire 5 made of Pt, Ni or the like is inserted into the central passage of this insulating tube 67. This lead wire 5 is electrically connected to a porous reference electrode 2 through conductive paste 66 made of Pt, Ni or the like, and the reference electrode 2 is connected to a main measuring apparatus through the lead wire 5. The insulating tube 67 is fixed to the holder 60 by glass sealing material 65. Further, a space between the insulating tube 67 and the holder 60 is sealed with this glass sealing material 65 to form a gas-tight seal from the outside atmosphere.

In between the sensor element 1 in the holder 60 and the ceramic insulating tube 67, solid reference material 64 which is used as the reference of galvanic electromotive force is filled so that it contacts with the reference electrode 2. As this solid reference material 64, hydroxyapatite, aluminum phosphate and the like can be used.

Next, the operation of thus constructed sensor probe will be described. By dipping the lower end of the sensor element 1 made of proton conductive solid reference material into molten metal (not shown in this drawing), a space surrounded by the sensor element 1 and the surface of molten metal is formed in the sensor element 1. Only a lower part of the sensor element 1 is dipped into molten metal, but most part of the measuring electrode 3 is placed in said space.

Thereby, hydrogen dissolved in molten metal reaches in equilibrium with hydrogen gas in the space surrounded by the sensor element 1 and molten metal, and the relationship between the hydrogen concentration S in molten metal and the hydrogen partial pressure $P_{H2}$ in said space can be expressed by the equation (3). Therefore, the electromotive force E generated between the reference electrode 2 and the measuring electrode 3 contacting with gas in said space is detected using solid reference material 11 as the reference of galvanic electromotive force, and the hydrogen partial pressure $P_{H2}$ over the surface of molten metal is obtained from this galvanic electromotive force according to the equation (1). Then, the hydrogen concentration S in molten metal is calculated from this hydrogen partial pressure $P_{H2}$ using said equation (3). Thus, hydrogen concentration in molten metal can be measured without dipping the formed part of the measuring electrode 3 of the sensor element 1, i.e. the electromotive force measuring part, into molten metal. Therefore, corrosion of the sensor element 1 by molten metal can be avoided, and dissolved hydrogen concentration can be continuously measured for long period.

Then, manufacturing of the sensor probe according to the embodiment shown in FIG. 16 and results of determination of hydrogen concentration in molten metal will be described. First, the alumina holder 60 was inserted into the sensor element 1 manufactured as described above, and the holder 60 and the element 1 were fixed with powdered glass sealing material 7 (composition: $Na_2O_3 \cdot B_2O_3 \cdot SiO_2$; thermal expansion coefficient: $9.5 \times 10^{-6}$; softening point: 695° C.; fluidization point: 880° C.). Then, as solid reference material 64, a mixture of $AlPO_4$ and $La_{0.4}Sr_{0.6}CoO_{3-x}$ powders was filled in the holder 60. An alumina insulating tube 67 inserted with Pt lead wire 5 and painted with Pt paste 66 on its lower end was inserted into the holder 60 and fixed to the holder 60 with powdered glass sealing material 65. And, the lead wire 5 was electrically connected to the reference electrode 2 by Pt paste 66 on the lower end of the insulating tube 67. Thus constructed sensor probe was heated in an electric furnace to fuse powdered glass sealing material 7 and 65. The hydrogen concentration in molten metal was measured using thus manufactured sensor probe as shown in FIG. 4. Effects similar to those shown in FIGS. 5 and 6 could be obtained.

Figure 17:
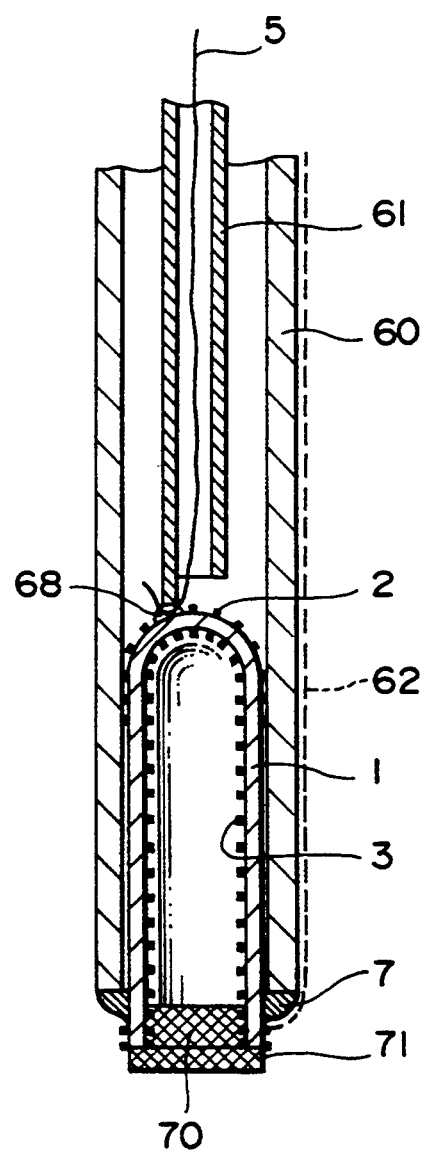
FIG. 17 is a sectional view of a sensor probe for measuring dissolved hydrogen concentration provided in accordance with the eighth embodiment of the present invention.

Then, referring to FIG. 17, the eighth embodiment of this invention will be described. In FIG. 17, all parts identical to those used in FIG. 14 identified with the same numerals used for FIG. 14 and detail description was omitted.

To the lower opening part of a sensor element 1, is attached with a silicon carbide (SiC) filter 70 as a plug for the opening part of the sensor element 1. This filter 70 is fixed to the sensor element 1 by ceramic adhesive 71. This filter 70 is made of porous material with the average pore size of 30 μm or less.

Next, the operation of thus constructed sensor probe will be described. By dipping a part including the silicon carbide filter 70 into molten metal (not shown in this drawing), a space surrounded by the filter 70 is formed in the sensor element 1 so that the space is placed lower level than the surface of molten metal. By doing this, permeability of molten metal into said space is prevented by the filter 70, only this space contacts with molten metal through the filter 70 and thereby the measuring electrode 3 of the sensor element 1 contacts with gas in the space.

Thus, hydrogen concentration in molten metal reaches in equilibrium with hydrogen gas in the space surrounded by the sensor element 1. Therefore, by measuring the hydrogen partial pressure $P_{H2}$ in this space by the sensor element 1 using galvanic electromotive force, the hydrogen concentration S dissolved in molten metal can be obtained as mentioned above based on the relationship between the hydrogen concentration S in molten metal and the hydrogen partial pressure $P_{H2}$ in said space. Thus, hydrogen concentration in molten metal can be measured without dipping the sensor element 1 into molten metal. Therefore, corrosion of the sensor element 1 by molten metal can be avoided, and dissolved hydrogen concentration can be continuously measured for long period.

Figure 18:
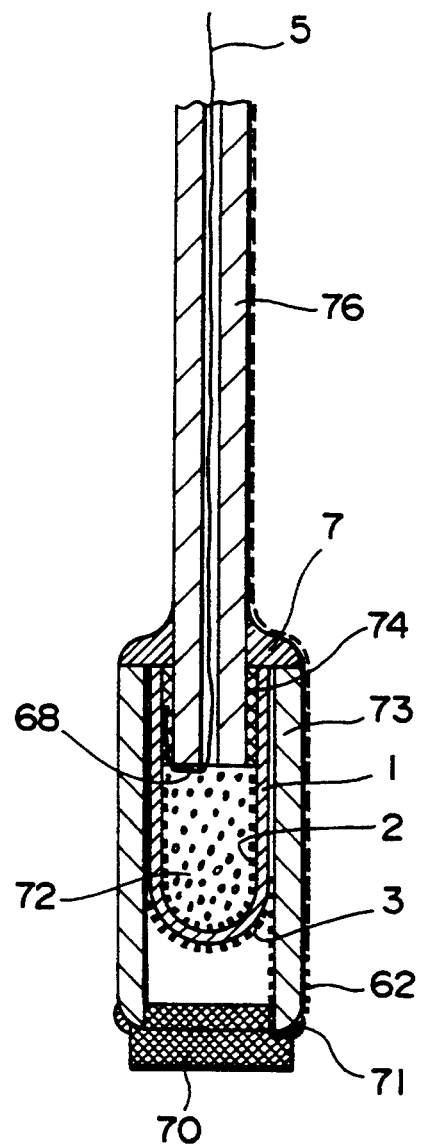
FIG. 18 is a sectional view of a modified form of the sensor probe shown in FIG. 17.

Then, referring to FIG. 18, a modified form of this embodiment will be described. In FIG. 18, all parts identical to those used in FIG. 17 are identified with the same numerals used for FIG. 17, and detail description was omitted. In the upper half of a sensor element 1, is inserted with a part of a ceramic insulating tube 76 to hold the sensor element 1, and the sensor element 1 and the ceramic insulating tube 76 are fixed with ceramic adhesive 74. In the central passage of this insulating tube 76, a lead wire 5 made of Pt, Ni or the like is inserted. This lead wire 5 is electrically connected to a reference electrode 2 on the inner surface of the sensor element 1 through metal paste 68 made of Pt, Ni or the like.

In the space enclosed by the insulating tube 76 in the sensor element 1, solid reference material 72 as the reference for galvanic electromotive force is filled to contact with the reference electrode 2. As this solid reference material 72, hydroxyapatite, aluminum phosphate and the like can be used.

The sensor element 1 is inserted with a ceramic sleeve 73 with openings at both sides. The upper end of this sleeve 73 is placed at the same level as the upper end of the sensor element 1, but its lower end is slightly extruding downwards than the lower end of the sensor element 1. On the upper parts of both sleeve 73 and sensor element 1, glass sealing material 7 is placed to keep in gas-tight the upper parts of the sleeve 73 and the sensor element 1 as well as the outer part of the ceramic insulating tube 76. On the inner and outer surfaces of the sleeve 73, lead 62 made of conductive paste is painted, and this lead 62 is connected to the measuring electrode 3 on the outer surface of the sensor element 1. Thereby, the measuring electrode 3 is connected to a signal processor through this lead 62.

A porous ceramic filter 70 made of silicon carbide (SiC) with poor wettability to molten metal is attached to the lower opening part of the sleeve 73. Next, the operation of thus constructed sensor probe will be described. First, by dipping the sleeve 73 and the filter 70 into molten metal (not shown in this drawing), a space surrounded by the sleeve 73, the sensor element 1 and the filter 70 is placed lower level than the surface of molten metal. By doing this, said space contacts with molten metal through the filter 70, and thereby the measuring electrode 3 of the sensor element 1 contacts with this space.

Thus, hydrogen concentration in molten metal reaches in equilibrium with hydrogen gas in said space, and the hydrogen partial pressure $P_{H2}$ in this space can be measured by the sensor element 1 using galvanic electromotive force. However, solid reference material 72 contacting with the reference electrode 2 in the sensor element 1 is used as the reference for galvanic cell. Then, based on the relationship between the hydrogen concentration S in molten metal and the hydrogen partial pressure $P_{H2}$ in said space as expressed by the equation (3), the hydrogen concentration in molten metal 5 can be measured without direct contact of the sensor element 1 with molten metal as mentioned in the first embodiment.

Moreover, in the method of use of the sensor probe shown in FIGS. 17 and 18, it is not needed to deeply dip either the sensor element 1 or the sleeve 73 into molten metal. It suffices to dip the sensor probe in molten metal to the depth that allows the porous filter 70 to be completely immersed and the space contacting with the measuring electrode 3 to be kept in gas-tight by the filter 70.

Then, manufacturing of the sensor probe according to the embodiment shown in FIG. 18 and results of determination of hydrogen concentration in molten metal will be described. First, as solid reference material 72, a mixture of $AlPO_4$ and $La_{0.4}Sr_{0.6}CoO_{3-x}$ powders was filled in the sensor element 1, and the alumina insulating tube 76 inserted with Pt lead wire 5 and painted with Pt paste 68 on its lower end was inserted into the sensor element 1 and fixed with ceramic adhesive 74. Then, the sensor element 1 was attached to the alumina sleeve 73 about 10 mm longer than the sensor element 1, and they were fixed to the alumina insulating tube 76 with powdered glass sealing material 7 (composition: $Na_2O_3.B_2O_3.SiO_2$; thermal expansion coefficient: $9.5 \times 10^{-6}$; softening point: 695° C.; fluidization point: 880° C.) to seal the openings. To the lower end of the sleeve 73, was attached the porous silicon carbide filter 70 with the average pore size of 15 μm and fixed to the opening part of the sensor element 1 with ceramic adhesive 71. Thus constructed sensor probe was heated in an electric furnace (heating and cooling rate: 5° C./minute; maintained at 850° C. for 10 minutes) to fuse powdered glass sealing material 7, then ceramic adhesive 71 and 74 were solidified. In this embodiment, the hydrogen concentration in molten metal was measured as shown in FIG. 4. As result, similar measurements as shown in FIGS. 4 and 5 could be obtained.

Figure 19:
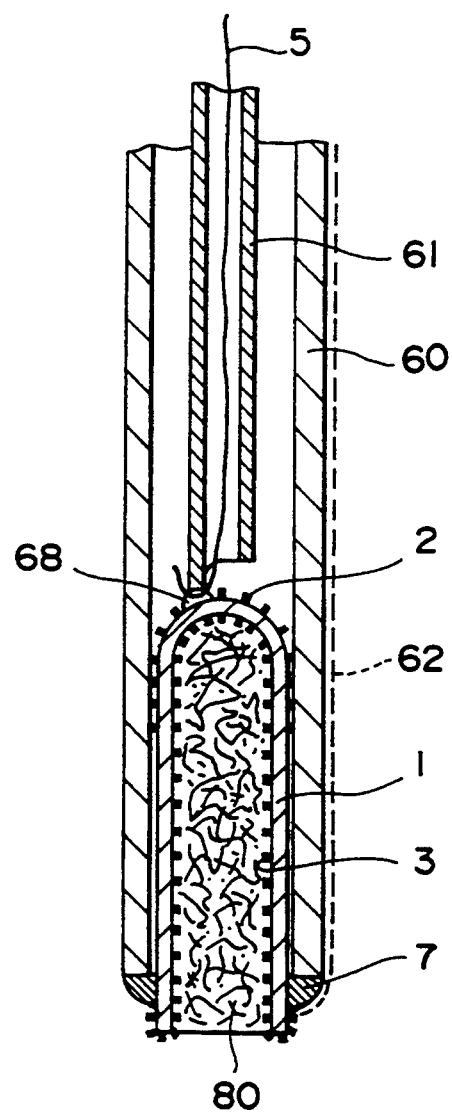
FIG. 19 is a sectional view of a sensor probe for measuring dissolved hydrogen concentration provided in accordance with the ninth embodiment of the present invention.

Then, referring to FIG. 19, the ninth embodiment of this invention will be described. In FIG. 19, all parts identical to those referred in FIG. 17 are identified by the same numerals as used in FIG. 17, but detail description will be omitted.

In this embodiment, a sensor element 1 is filled with ceramic fiber 80 such as alumina fiber and the like.

Then, the operation of thus constructed sensor probe will be described. First, a ceramic tube 60 is dipped into molten metal (not shown in FIG. 19) so that a space separated from the outer atmosphere is formed in the sensor element 1. Because ceramic fiber 80 is filled in this sensor element 1, molten metal does not permeate into this sensor element 1, but gas can permeate into this sensor element 1. Because this gas phase is contacting with molten metal, hydrogen concentration in the gas phase reaches in equilibrium with hydrogen concentration in molten metal. Therefore, as mentioned above, the hydrogen concentration in molten metal can be measured without directly contact of the sensor element 1 with molten metal. Thus, corrosion of the sensor element 1 by molten metal can be avoided, and dissolved hydrogen concentration can be continuously measured for long period.

Figure 20:
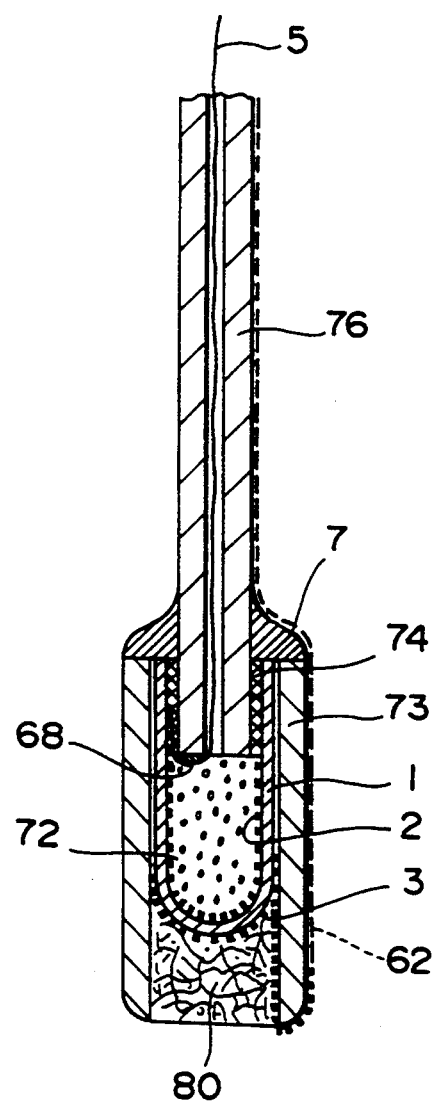
FIG. 20 is a sectional view of a modified form of the sensor probe shown in FIG. 19.

Next, referring to FIG. 20, a modified form of this embodiment will be described. In FIG. 20, all parts identical to those referred in FIGS. 18 and 19 are identified by the same numerals as used in FIGS. 18 and 19, but detail descriptions will be omitted.

In this embodiment, ceramic fiber 80 such as alumina fiber and the like is filled in the extruded part of a sleeve 73.

Then, the operation of thus constructed sensor probe will be described. First, the lower part of the sleeve 73 is slightly dipped into molten metal (not shown in FIG. 20). Thereby, the space surrounded by the sleeve 73 and the sensor element 1 contacts with molten metal. Therefore, the space in the ceramic fiber 80 is filled with gas phase contacting with this molten metal, and the measuring electrode 3 of the sensor element 1 contacts with this gas phase.

Then, hydrogen concentration in molten metal can be measured using solid reference material 72 as the reference for galvanic cell without direct contact of the sensor element 1 with molten metal. Therefore, corrosion of the sensor element 1 by molten metal can be avoided, and dissolved hydrogen concentration can be continuously measured for long period.

Then, manufacturing of sensor probe according to the embodiment shown in FIG. 20 and results of measurement of hydrogen concentration in molten metal will be described. In this sensor probe, alumina fiber 80 was filled in the lower part of the sleeve 73 instead of the filter 70. This sensor probe also provided accurate measurements of hydrogen concentration in aluminum molten metal.

Figure 21:
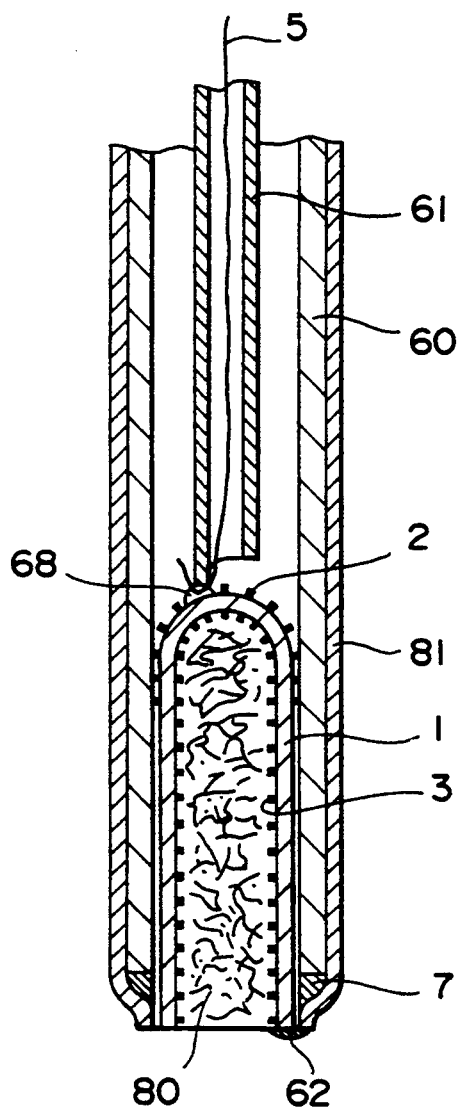
FIG. 21 is a sectional view of a sensor probe for measuring dissolved hydrogen concentration provided in accordance with the tenth embodiment of the present invention.

Then, referring to FIG. 21, the tenth embodiment of this invention will be described. In FIG. 21, all parts identical to those shown in FIG. 19 are identified with the same numerals as shown in FIG. 19 without detail descriptions. In this embodiment, metal film 81, in 10 to 1000 μm thick, made of Pt, Pd, Rh, Ni, Al and the like with superior wettability to molten metal is formed on the outer surface of a ceramic insulating tube 60 and the surface of glass sealing material 7. This metal film 81 can be formed also by seizure of the ceramic tube 60 painted with metal paste on its outer surface in an electric furnace. Also, the metal film 81 can be formed on the outer surface of the ceramic tube 60 by spraying said melted metal on the surface of ceramic tube.

Then, the operation of thus constructed sensor probe will be described. First, by dipping the ceramic insulating tube 60 into molten metal (not shown in the drawing), a space separated from the outer atmosphere is formed in the sensor element 1. In this case, because the metal film 81 is formed on the outer surface of the sensor probe, the wettability of the sensor probe to molten metal is good and the penetration of the outside air into the sensor element 1 through the metal film 81 on the surface of this sensor probe can be prevented. Therefore, the space in the sensor element 1 can be completely separated from the outside atmosphere. Because ceramic fiber 80 is filled in this sensor element 1, molten metal can not permeate and only gas phase can permeate into this sensor element 1. Also, this gas phase is contacting with molten metal, therefore the hydrogen gas concentration in gas phase reaches in equilibrium with the hydrogen concentration in molten metal.

Thereby, the hydrogen concentration in molten metal can be measured without direct contact of the sensor element 1 with molten metal. Therefore, corrosion of the sensor element 1 can be avoided and dissolved hydrogen concentration can be continuously measured for long period.

Figure 22:
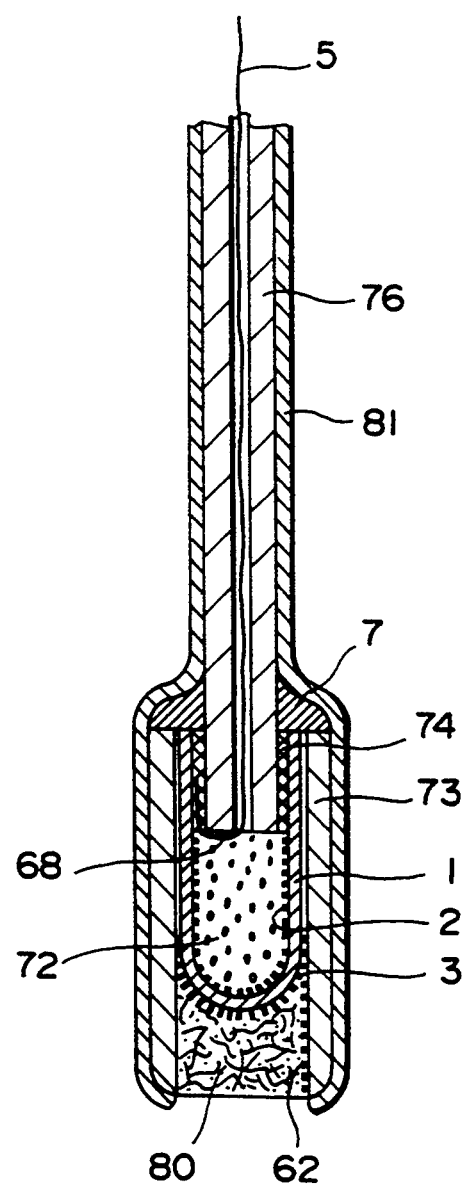
FIG. 22 is a sectional view of a modified form of the sensor probe shown in FIG. 21.

Then, referring to FIG. 22, a modified form of this embodiment will be described. In FIG. 22, all parts identical to those shown in FIGS. 20 and 21 are identified with the same numerals as used in FIGS. 20 and 21 without detail description.

In this embodiment, on the outer surfaces of a sleeve 73 and a ceramic insulating tube 76 with identical structures with the sensor probe shown in FIG. 20, metal film 81 with superior wettability to molten metal is formed in the same manner as the embodiment shown in FIG. 21.

Then, the operation of thus constructed sensor probe will be described. First, the lower end of the sleeve 28 is dipped into molten metal (not shown in the drawing). Thereby, a space surrounded by the sleeve 73 and the sensor element 1 contacts with molten metal. Therefore, gas phase contacting with this molten metal saturates in the ceramic fiber 80, and the measuring electrode 3 of the sensor element 1 contacts with this gas phase.

Thereby, hydrogen concentration in molten metal can be measured in the same manner as the embodiment shown in FIG. 20. In this embodiment, penetration of the outside air into the sensor probe can be completely prevented in the same manner as the embodiment shown in FIG. 21 because the metal film 81 with superior wettability to molten metal is formed on the outer surface of the sensor probe.

Then, the sensor probe of this embodiment shown in FIG. 22 was manufactured, and hydrogen concentration in molten metal was measured. In this embodiment, hydrogen concentration in molten metal could be accurately measured.

What is claimed is:

1. A sensor probe for measuring hydrogen concentration in molten metal, comprising:
   a tubular sensor element made of proton conductive solid electrolyte having a perovskite structure and enclosed at one end,
   a reference electrode constituted of a porous material formed on the inner surface of said sensor element,
   a measuring electrode constituted of a porous material formed on the outer surface of said sensor element,
   sealing material separating and preventing gas communication between said reference electrode and said measuring electrode,
   a ceramic sleeve fixed on the outer surface of said sensor element so as to create a gas space in the sleeve between the molten metal and the measuring electrode, thereby at least a part of said measuring electrode on the outer surface of said sensor element being located in the gas space, said sleeve, in a portion thereof which protrudes from said sensor element, being filled with a ceramic fiber to prevent the penetration of molten metal into the sleeve, and
   a metal film having a thickness of at least 3 $\mu$m covering the outer surface of a portion of said sleeve to be dipped into said molten metal to increase the wettability of said sleeve with said molten metal.

2. The sensor probe according to claim 1, further comprising:
   means for supplying a reference gas to said reference electrode formed on the surface of said sensor element as a reference for galvanic electromotive force.

3. The sensor probe according to claim 1, further comprising:
   a solid reference material as a reference for galvanic electromotive force, located in said sensor element and contacting said reference electrode.

4. A sensor probe for measuring hydrogen concentration in molten metal, comprising:
   a tubular sensor element made of proton conductive solid electrolyte having a perovskite structure and enclosed at one end with an opening at the other end, said sensor element being filled with a ceramic fiber which prevents penetration of molten metal thereinto,
   a reference electrode constituted of a porous material formed on the outer surface of said sensor element,
   a measuring electrode constituted of a porous material formed on the inner surface of said sensor element,
   a sleeve in which said sensor element is fitted in such a way that the opened end of said sensor element slightly protrudes from said sleeve, a portion of said sleeve and said sensor element being covered by a metal film having a thickness of at least 3 $\mu$m which increases the wettability of said sleeve and said sensor element to molten metal when said sleeve is immersed into said molten metal, and
   a sealing member separating and preventing gas communication between said reference electrode and said measuring electrode.

5. The sensor probe according to claim 4, further comprising:
   means for supplying a reference gas to said reference electrode as a reference for galvanic electromotive force by introducing said reference gas into said sleeve.

6. The sensor probe according to claim 4, further comprising:
   a solid reference material as a reference for galvanic electromotive force, located in said sleeve and contacting said reference electrode.

* * * * *